US012790606B2

(12) United States Patent
Voinnet et al.

(10) Patent No.: US 12,790,606 B2
(45) Date of Patent: Nov. 10, 2026

(54) METHOD AND KIT FOR THE PURIFICATION OF FUNCTIONAL RISC-ASSOCIATED SMALL RNAS

(71) Applicant: ETH Zürich, Zürich (CH)

(72) Inventors: Oliver Voinnet, Zürich (CH); Thomas Grentzinger, Züruch (CH); Grégory Schott, Gockhausen (CH)

(73) Assignee: ETH Zürich, Zürich (CH)

( * ) Notice: Subject to any disclaimer, the term of this patent is extended or adjusted under 35 U.S.C. 154(b) by 1272 days.

(21) Appl. No.: 17/603,908

(22) PCT Filed: Apr. 15, 2020

(86) PCT No.: PCT/EP2020/060600

§ 371 (c)(1),
(2) Date: Oct. 14, 2021

(87) PCT Pub. No.: WO2020/212428

PCT Pub. Date: Oct. 22, 2020

(65) Prior Publication Data

US 2022/0220467 A1 Jul. 14, 2022

(30) Foreign Application Priority Data

Apr. 15, 2019 (EP) .................................... 19169263

(51) Int. Cl.
*C12N 15/10* (2006.01)

(52) U.S. Cl.
CPC ................................. *C12N 15/101* (2013.01)

(58) Field of Classification Search
CPC .................................................... C12N 15/101
USPC ......................................................... 536/25.4
See application file for complete search history.

(56) References Cited

FOREIGN PATENT DOCUMENTS

| | | | |
|---|---|---|---|
| AU | 2007202668 | A1 | 7/2007 |
| CN | 1876820 | A | 12/2006 |
| WO | WO-2010/033652 | A1 | 3/2010 |

OTHER PUBLICATIONS

Omarov et al. An in vitro reprogrammable antiviral RISC with size-preferential ribonuclease activity. Virology 490(2016)41-48. (Year: 2016).*
Rudel et al. A multifunctional human Argonaute2-specific monoclonal antibody. RNA (2008), 14:1244-1253. (Year: 2008).*
Bio-Rad, Introduction to Multimodal or Mixed-Mode Chromatography. Bio-Gel® HT hydroxyapatite.p. 1-8 (accessed in Jun. 2025) (Year: 2025).*
Xiaoke, "Experiment 54 Conventional DNA Recovery," Chapter 7, Comprehensive Experiments in Bioengineering, China Press of Chinese Medicine, Beijing, Specialized Textbook for Experimental Training in Higher Colleges of Traditional Chinese Medicine, 4 pages (2016).
Grentzinger et al., "A user-friendly chromatographic method to purifyt small regulatory RNAs," Methods 67:91-101 (2014).
Bellutti et al., "Identification of RISC-Associated Adenoviral MicroRNAs, a Subset of Their Direct Targets, and Global Changes in the Targetome upon Lytic Adenovirus 5 Infection," Journal of Virology 89(3):1608-1627 (2015).
International Search Report and Written Opinion from International Application No. PCT/EP2020/060600 dated May 13, 2020.

* cited by examiner

*Primary Examiner* — Yih-Horng Shiao
(74) *Attorney, Agent, or Firm* — MARSHALL, GERSTEIN & BORUN LLP

(57) ABSTRACT

The invention relates to methods and kits for the purification of functional RISC-associated small RNAs in organisms, organs, tissues, cells or biological fluids.

10 Claims, 15 Drawing Sheets

METHOD AND KIT FOR THE PURIFICATION OF FUNCTIONAL RISC-ASSOCIATED SMALL RNAS

CROSS-REFERENCE TO RELATED APPLICATIONS

This application is a U.S. National Phase of International Application No. PCT/EP2020/060600, filed Apr. 15, 2020, which claims priority to European Application No. 19169263.1, filed Apr. 15, 2019, which are incorporated herein by reference in their entirety.

FIELD OF THE INVENTION

The invention relates to methods and kits for the purification of functional RISC-associated small RNAs in all organisms, organs, tissues, cells or biological fluids.

BACKGROUND OF THE INVENTION

In the vast majority of eukaryotic organisms, RNA silencing is a fundamental gene regulation mechanism that also serves essential defensive functions against invasive nucleic acids such as transposons and viruses. In all eukaryotic organisms studied so far, the core component of RNA silencing is the RNA induced silencing complex (RISC), composed of an Argonaute-family (AGO) protein associated with a small RNA (sRNA), 17-33 nucleotides (nt) in length.

Endogenous microRNAs

In healthy organisms, most sRNAs have cellular origins, in which case they are encoded at specific loci that generate them via various mechanisms. One of these mechanisms, which spawns a large family of such endogenous RNAs called microRNAs (miRNAs), involves highly conserved RNase-III proteins in the Dicer family. miRNAs, 21-24 nt in size, are encoded by specific nuclear genes located between protein-coding genes or in introns. MIRNA genes encode non-coding primary transcripts (the pri-miRNAs) that invariably contain a double-stranded RNA (dsRNA) stem-loop structure. A shorter derivative of the pri-miRNAs, called the miRNA precursor or pre-miRNA, corresponds to the dsRNA stem-loop structure and is cut at a precise position by Dicer to generate a dominant, mature miRNA duplex. Upon incorporation into one or several AGO effector proteins, one strand of the duplex is selected as guide strand while the complementary strand, called passenger strand or miRNA*, is degraded. The resulting miRNA-RISC then scans the cell's transcriptome for mRNAs exhibiting partial or extended sequence complementarity to the miRNA, and subsequently executes post-transcriptional RNA silencing of these mRNAs via various means.

These include endonucleolytic cleavage (called slicing) through the nuclease core contained by many—albeit not all—AGO proteins, and/or translational repression via various possible mechanisms almost invariably accompanied by modest but consistent accelerated mRNA decay.

Circulating miRNAs

Over the past 10 years, it has been realized that a potentially large array of miRNAs is found in various (but usually very small) quantities in several mammalian body fluids including blood, lymph, milk, saliva and urine. miRNAs are particularly and surprisingly stable in the human plasma for as yet unspecified reasons. The exact origin of these miRNAs also remains a matter of debate: they may be found in apoptotic bodies derived, for instance from dead cells, and/or be actively secreted in micro-vesicles or exosomes typically derived, for example, from immune cells or produced at high levels in tumors. Independently of their origin, specific state or putative physiological roles, the identity and quantity of body fluid-borne miRNAs, and in particular blood-borne miRNAs, can be potentially used as diagnosis- and prognosis-enabling features for several diseases and pathological conditions in both human health and veterinary applications.

Virus-Encoded miRNAs

Analyses of differentiated mammalian cells infected by DNA viruses, mostly herpesviridae (e.g. Herpes simplex virus—HSV1/2, Epstein-Barr virus—EBV, cytomegalovirus—CMV, Kaposi sarcoma associated herpes virus—KHSV), which are characterized by their very large DNA genomes, have revealed that such viruses encode their own suite of miRNAs. These are produced upon transcription of viral genomes in the nucleus, by usurping the host miRNA machinery. Unlike virus-derived small interfering (vsiRNAs) which are turned against the invader, virus-derived miRNAs play important beneficial roles for the viruses from which they derive, including evasion of host immune responses, regulation of viral protein abundance, or entry of the virus into a persistent as opposed to a lytic infection state. Several virus-derived miRNAs have been found at physiological concentrations in extracellular vesicles secreted from infected cells and may thus function as gene expression regulators upon their uptake in cells surrounding the infection. Like their host-encoded counterparts, they may also be found in the blood and perhaps other body fluids and could be used as diagnostics of infections, although the usually latent state of herpesviridae is not favorable to their detection given the difficulties already encountered in detecting cellular miRNAs in body fluids. Virus-derived miRNAs represent potential targets for treatments, particularly in the case of KSHV, which is one the primary cause of death in immuno-compromised patients such as those affected by AIDS. It is currently unclear if the current techniques of miRNA profiling have unraveled the full cohort of virus-encoded miRNAs produced from these DNA viruses, because, as stated above, they are mostly in a latent state (and hence poorly transcribed in vivo while they are otherwise studied mostly in selected cell types in vitro. Circumstantial evidence points to the possible existence of miRNA being also encoded by at least some RNA viruses.

Small Interfering RNAs

Other Dicer-dependent sRNAs also have a foreign origin. In plants, invertebrates and at least some mammalian cells, long dsRNA, an almost invariable product of virus replication, is cellularly detected by Dicer-like proteins and converted into small interfering RNAs (siRNAs). Unlike discrete miRNAs, these virus-derived siRNAs, or vsiRNAs, are generated as populations produced by consecutive cuts along the dsRNA in a manner that often defines a specific dominant sequence register, a Dicer processing readout known as "phasing". Although their biogenesis is distinct from that of miRNAs, siRNAs nonetheless associate with one or several AGO proteins to form antiviral RISCs targeted against the viral RNA themselves, which they destroy via slicing and/or, possibly, translational repression. This antiviral RNA silencing response is unique in that it is purely innate, i.e., it can potentially adapt to every virus. Indeed, it is exclusively programmed by structural and nucleotide sequence features of viral genomes. In plants and some invertebrates, this response also has a non-cell autonomous component and moves ahead of the virus to immunize non-infected cells located away from the infection front. Antiviral RNAi also operates in vivo and in vitro in some mammalian cells but not others for reasons that currently remain elusive. In principle, given the high replication rates of most viruses, abundant vsiRNAs in infected tissues can be used to diagnose a specific viral disease or even a specific strain of a given virus because sections of full viral genomes can now be reconstituted by contiguing vsiRNAs that overlap in sequence. Alternatively, specific vsiRNAs can be used as disease markers via more targeted approaches.

Heterochromatic siRNAs and Other Endogenous siRNAs siRNAs are also not necessarily of viral origin since analyses in fission yeast, other fungi, plants, nematodes, *Drosophila* and possibly a multitude of additional organisms, have unraveled a plethora of endogenous siRNAs. These so called endosiRNAs derive mostly from transposable elements (TEs) and DNA repeats and promote chromatin condensation and transcriptional gene silencing at these loci, thereby possibly contributing to genome integrity maintenance. Other types of endosiRNAs also accumulate in plants, worms and flies, where they have various developmental and basic gene regulatory roles. EndosiRNAs have been detected in the mammalian germline, chiefly in oocytes, as well as in embryonic stem cells. Whether they accumulate in vivo in other cell types, tissues, organs or body fluids is yet to be determined.

PIWI-Associated sRNAs (piRNAs) and Scan RNAs (scnRNAs)

A species of germline-specific sRNAs that associate with AGO-like proteins known as PIWI proteins was discovered in flies and later, worms and mammals, but not in plants or fungi. piRNAs target transposons in the germline at both transcriptional (histone methylation) and post-transcriptional (via slicing operated by the PIWI proteins) levels. In flies these sRNAs also play essential roles in the zygote, which is protected by maternally-deposited PIWI-bound piRNAs against the potentially detrimental activity of transposons brought by the male genome. Defects in the piRNA pathway usually cause aberrant germline development in mammals and, in flies, hybrid dysgenesis.

Finally, variants of piRNAs have been detected in ciliates (e.g. Paramecium, Tetrahymena) in which a complex population of 25-29-nt scan RNAs (scnRNAs) accumulate during early meiosis. These scnRNAs have homology to all types of germline sequences found in the micronucleus and are used, upon their loading into PIWI-like proteins, to promote physical DNA excision of foreign sequences (usually transposons and repeats) from progeny somatic macronuclei. scnRNAs are produced from long dsRNA by Dicer-like proteins and have been so far only detected in protozoans.

Standard Methods for sRNAs Detection and Analysis

Historically, methods for detecting known siRNA in all organisms are based on northern analysis, which involves the separation of low molecular weight (LMW) RNA species from total RNAs extracted from whole organisms or specific organs, tissues or cell types on polyacrylamide gels. The gel is then blotted onto a nylon membrane that is subsequently subjected to crosslinking and hybridized with DNA-or RNA-based probes complementary to the sRNA(s) of interest. These probes are usually labeled with radioactive isotopes although other, less sensitive methods exist. Single species of miRNAs are usually detected with complementary, end-labeled oligonucleotides, but these usually cannot discriminate between the many miRNA isoforms and paralogs found in various species including of plants and mammals, which often differ by only one or a few nucleotides. Unlike the discrete miRNA species, siRNAs accumulate as populations and individually at low to very low abundance. Therefore, to detect the population rather than specific members of the bulk of siRNAs derived, say from a transposon, a virus, or an endogenous locus, long random-primed DNA probes are employed. The drawback of this approach is that information on individual siRNA species is not accessible. Another common drawback of northern analysis of both siRNA populations and single miRNA species is the limit of detection provided by the technique: low abundant sRNA species are often undetectable, even when large quantities of total, or even specifically enriched LMW RNAs (dozens of micrograms), are employed.

An alternative technique for detecting known sRNAs species, used mostly for miRNAs, relies on quantitative reverse transcription PCR (RT-qPCR) performed with specifically designed oligonucleotides. Compared to northern analysis, RT-qPCR-based detection of sRNAs is highly quantitative, extremely sensitive (only 1-10 ng of total RNA is needed) such that it allows detection of sRNAs from groups of cells or even single cells. However, like the probes used in northern analyses, RT-qPCR probes do not always discriminate between specific miRNA isoforms and paralogs differing by only a few nucleotides. This method is also barely efficient, and indeed seldom used, to quantify single siRNAs from the populations from which they derive.

As an alternative to RT-qPCR, microarrays encompassing all or a fraction of known miRNAs in a given species can also be used to quantify single miRNA species. In this case, total RNA or the specifically prepared LMW RNA fraction is labelled with fluorescent dyes (e.g. Cyanine 3-pCp) at the 3' ends and hybridized to the microarray. This method offers a sensitivity comparable to that of RT-qPCR, with a wide dynamic range.

A major common drawback of northern, RT-qPCR and microarray-based sRNA detection methods, however, is that they all rely on the prior knowledge of validated sRNA species. Therefore, none of these methods allows an unbiased exploration of the sRNA content of an organism, organ, tissue of cell type of interest, let alone under biotic/abiotic stresses, cellular metabolism dysregulation or disease contexts. Yet, such contexts are known to change—sometimes profoundly—the sRNA landscape of said organism/organ/tissue/cell type and to induce accumulation of specific sRNAs that are often below detection levels in healthy or unstressed cells.

Because of the impact of sRNA biology in fundamental and applied research, various methods and protocols have been developed to access sRNAs in a multitude of organisms, organs, tissues and cell types via massive parallel sequencing, referred to here as "deep sequencing" or "deep-seq". Unlike the previously mentioned technologies, deep-seq allows access to sRNA populations at the genome scale without any prior knowledge of their sequences. All current sRNA deep-seq technologies affordable to academic, clinical and corporate research are based on 3' and 5' adaptors ligation to the sRNAs. These allow reverse transcription of RNA into cDNA, followed by several PCR amplification cycles to generate a so called "sRNA library". The library is then subjected to deep-seq at varying depths depending on the platform used (e.g. 454, SOLID, Illumina) generating sequencing files from which genome-wide sRNA information is extracted upon curation. Further computer-based analyses then allow qualitative and quantitative sRNA sorting in any given sample, as well as differential analysis between samples or cohorts. Reproducible variations to sRNA repertoires induced, e.g., by a specific developmental, stressed or pathological state can thus be identified, from which "elite" sRNAs (mostly miRNAs in mammals) can be selected as potential biomarkers of these particular cellular states, physiological or pathological conditions.

However, nearly all embodiments of total sRNA sequencing from samples require prior size separation from longer RNAs via various means, in order to avoid the cloning of sometimes abundant, tRNAs, rRNA or mRNA breakdown products that populate the <70-nt fraction. This is particularly important in some biological models including, for instance, plants or *Drosophila,* in which direct cloning of sRNAs after e.g. Trizol extraction results in libraries that are replete with contaminants and, as such, mostly unusable. The same problem applies to biological fluids (e.g. plasma) replete in RNA contaminants with comparatively little amounts of bona fide sRNAs. Trizol-extracted sRNA libraries without size selection prepared from other "normal" tissues from several organisms may be acceptable, albeit nearly always of suboptimal quality. Although avoided or bypassed by expert laboratories for preliminary, routine analysis or for fear of sample loss (see below), the gold standard for total sRNA sequencing—used by most commercial providers—entails in-gel size-separation prior to library cloning and sequencing. Laborious and time consuming acrylamide gel-based separation remains the most robust technique although other methods have been developed commercially.

During this gel-based separation, total RNA is separated via electrophoresis on high-concentration polyacrylamide gel alongside an (often radio-labeled) RNA ladder used as a size reference. This enables excision of the part of the gel enriched for the cognate sRNA of interest (typically 18-25-nt for siRNAs and miRNAs; 27-32-nt for piRNAs and scnRNAs). The excised RNA is then re-extracted from the gel before the proper preparation of the library. The prolonged handling of samples through multiple tedious steps favors their degradation and that of longer, unrelated RNAs ending up as contaminants. In addition, a variable and generally important proportion of sRNA material is lost in the procedures, resulting in low-to-very low yields of total sRNAs. The inherent requirement for high amounts of starting biological material, typically in the range of several micrograms of total RNA, poses a considerable challenge for samples that are degradation-prone (e.g. biopsies), limited in quantity (e.g. embryos, ovaries) and/or in sRNA content (e.g. biological fluids). Due to its complexity, proneness to degradation and low yield, sRNA size selection and ensuing library preparation are often outsourced to specialized companies for the sake of reliability. Outsourcing of library preparation incurs high costs due to the manual labor involved, ironically often exceeding by up to one order of magnitude the continually decreasing costs of deep-seq reagents, and hence, of sequencing reactions per se.

Irrespective of their form, another major caveat of size selection procedures prior to sRNA library preparation is that degradation products of longer RNA and/or highly abundant RNA within the size range of interest (e.g. 2S rRNA in *Drosophila*) are poorly, if at all, separated. This usually results in sequence data being confounded by high background causing substantial amounts of false positives. In addition, such contaminants may occupy a substantial sequencing space. In *Drosophila,* the problem posed by the co-migrating 2S rRNA is such that it requires the use of yet another step, called ribodepletion, as part of the whole gel separation procedure prior to ligation, thus further increasing the risks of degradation of the sampled RNA. Despite ribodepletion, rRNA typically represents 20-40% of all sequencing reads from standard sRNA libraries in flies. Analyses focused on piRNAs, usually from dissected *Drosophila* ovaries, are somewhat more favorable in this regard because another step, this time called oxidization, enables removal of most of the rRNA remaining after ribodepletion, taking into account the unique 2'-O-methylated status of piRNAs, which protects them from periodate attack. The same step is usually employed for piRNA deep-seq analysis in the mammalian germline. The drawback, however, is that this added step requires even more handling of an RNA extracted from very limiting amounts of tediously isolated tissues (ovaries, testis) and thus increases even more the risk of degradation or the mere loss-of-material. Altogether, deep-seq of piRNAs from dissected fly ovaries can be considered as a benchmark for one of the most challenging setting for genome-wide or directed sRNA analyses because of low starting material quantity, tediousness, risk of degradation and high contamination.

In all organisms, dedicated AGO/PIWI proteins are loaded with specific sRNAs to execute particular biological functions. Therefore, for most applications, it is necessary to identify RISC-associated sRNAs rather than the general pool of sRNAs present in a sample of interest. Up to now, the most common way to address this necessity was the development of highly specific anti-AGO/PIWI antibodies amenable to immunoprecipitation (IP). After IP, the sRNA population bound to the AGO of interest is then phenol-extracted, cloned and subjected to deep-seq following the same procedure used in total sRNA sequencing. A major qualitative difference, however, is that the purification of AGO proteins with their cargoes enables a considerable enrichment in sRNAs against contaminating RNA or breakdown products. Currently, it is possible to operate adapter ligation, amplification and deep-seq directly (i.e. without size selection on gel) on RNA extracted from AGO/PIWI IPs.

Recently, an alternative method to AGO IP was developed based on the high affinity for human AGO2 displayed by a mammalian protein known as GW182 (or TNRC6) required for miRNA-mediated target regulation at the translational and mRNA decay levels. GW182 contains several repeated GW residues that form a domain known as "AGO-Hook". AGO-hooks are found in other organisms as well, where they may display high polymorphism in terms of the GW dyad density and spatial organization. In these organisms, AGO-hooks help attribute specialized functions to some—albeit not all—AGOs. In plants, for instance, a specific AGO-hook protein enables AGO4, AGO6 and AGO9 to access DNA to guide chromatin modification with heterochromatic siRNAs derived from transposons and repeats. Thus, one embodiment of gel-free sRNA separation entails the use of a short GW182-derived peptide fused to GST to bind with high affinity at least some AGO proteins complexed with sRNAs. This method is known as "AGO protein Affinity Purification by Peptides" (AGO-APP).

The main caveat of the AGO-APP method, which has greatly limited its widespread application for RISC isolation, is that only some AGOs display sufficient affinity for GW repeats to be pulled-down by the technique. Applied to plants, for instance, AGO-APP could significantly purify only 2 out of the 10 AGO proteins of *Arabidopsis.* The proficiency of AGO-APP is thus unpredictable and variable depending on intrinsic features of AGO proteins that influence their interaction with AGO-hooks. Across kingdoms some AGOs probably have not even evolved to interact with such proteins as part of the pathway(s) they are involved in.

IP-based sRNA sequencing is of major interest for many experimental applications. However, development of high quality AGO/PIWI antibodies amenable to IP may take years and such antibodies do not always discriminate individual members of large AGO/PIWI families often found within single organisms. In mammals, AGO IPs function well for AGO1 and AGO2 but are vastly suboptimal for AGO3 and AGO4 due the lack of suitable in-house or commercial antibodies. Moreover, AGO/PIWI antibodies do not often cross-react, even in related species, which usually confines the use of IP-coupled Deep-seq to model organisms. IPs are not only tedious, time-consuming and technically demanding, they also inherently rely on a preconceived idea of which AGO(s) is (are) present in any given sample, a knowledge only rarely available. Differences in AGO immunogenicity (and hence antibody efficacy/specificity), or the mere unavailability of IP-proficient antibodies, imply that the approach is naturally biased, poorly comparative between and within IPs of distinct AGOs, and generally poorly reflective of the complete portfolio of AGO sRNA cargoes present in the sample(s) of interest.

Another major constraint of both the IP and AGO-APP methods is that they are only adapted to laboratory work conducted with small amounts of samples. Indeed, due to their multi-step nature and high technicity (beads coupling, multiple washing, treatment with cleavage buffer for AGO-APP) as well as the involvement of long incubations at 4° C. (overnight with AGO-APP), neither are conceivably easily adaptable to medium/high-throughput settings such as those required for clinical explorations involving many samples from large patients' cohorts. Even for targeted applications involving small sample numbers, field agronomists, veterinarians or clinicians employ AGO-IP or AGO-APP reluctantly, which remain cumbersome and demanding for non-expert users.

OBJECTIVE TECHNICAL PROBLEM TO BE SOLVED

There is therefore a need for a fast, simple and reliable method for the purification of functional (i.e., AGO-loaded/RISC-associated) sRNAs which does not require previous knowledge of the sample's AGO(s) content and which can thus be applied irrespective of the organism, tissue, biological fluid or cell type of interest. Such a method should allow user-friendly, high throughput and high-quality purification of functional sRNAs regardless of RNA contaminants or of the RNA degradation status of the sample. Finally, to the method should allow robust sRNA isolation from notoriously recalcitrant tissues (e.g. starchy plants, serum and plasma) and/or from minute amounts of starting material.

SUMMARY OF THE INVENTION

The problem is solved by a method for the purification of RISC-associated sRNAs, comprising the following steps:

a) providing a native sample derived from a biological specimen containing RISC-associated sRNAs;
b) lysing the sample using a native lysis buffer;
c) selectively removing non-RISC associated nucleic acids from the lysate; and
d) collecting RISCs comprising RISC-associated sRNAs.

In another embodiment, the problem is solved by providing a kit for the purification of RISC-associated sRNAs, comprising a native lysis buffer;
an elution buffer; and
a column having a body comprising an anion exchange resin.

DETAILED DESCRIPTION OF THE INVENTION

Figure 1:
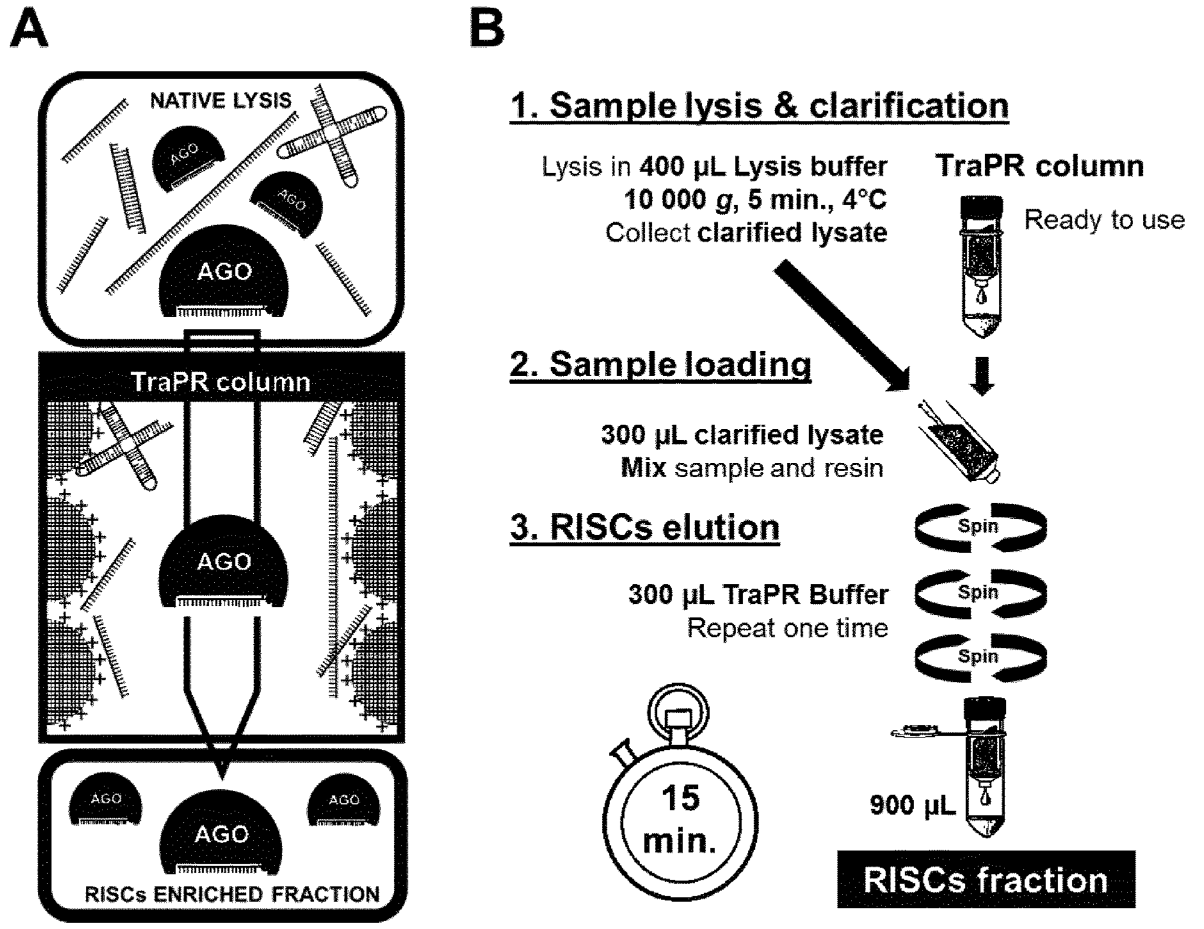
FIG. 1A shows the underlying principle of the method according to the invention. Native clarified lysate is mixed with a positively charged matrix, flow-through is collected and elution is performed using an increasing salt concentration. RISCs and their associated sRNA are eluted before at a given salt concentration whereas negatively charged free nucleic acids remain stuck on the column.
FIG. 1B shows a schematic overview of the method according to the invention. The method according to the invention requires three main steps: Native lysis of the sample and clarification, loading of clarified lysate onto the column and mixing with the anion exchange resin and elution of RISC-associated sRNAs using three short centrifugations. The procedure is routinely performed in 15 minutes.

In one aspect, the present invention relates to methods for the purification of RISC-associated sRNAs, comprising the following steps:

a) providing a native sample derived from a biological specimen containing RISC-associated sRNAs;
b) lysing the sample using a native lysis buffer;
c) selectively removing non RISC-associated nucleic acids from the lysate; and
d) collecting RISCs comprising RISC-associated sRNAs.

The method according to the invention is called TraPR, standing for Transkingdom rapid and affordable Purification of RISCs.

Herein, the term "sRNAs" relates to small RNA molecules with a length of 18 to 40 nucleotides. The term is intended to cover microRNA (miRNA), Piwi-interacting RNA (piRNA), small interfering RNA (siRNA), scan RNA (scnRNA). In particular, the term refers to any sRNA molecule functionally associated with an Argonaute (AGO)-family protein as part of a RISC which may be engaged in gene regulation. The terms "sRNA", "sRNA molecule" and "sRNAs" are used interchangeably.

The term "RISC-associated sRNAs" herein refers to sRNAs that are functionally incorporated into a RISC, e.g. via association with or loading onto an AGO-family protein. The term is not intended to cover free RNAs that do not interact with a RISC and/or are not loaded onto a RISC at the time of purification. RISC-associated sRNAs are the RNA type most interesting since their interaction with and loading onto an AGO-family proteins is a prerequisite for them to convey mRNA regulation. It is therefore highly preferable to isolate the RISC-loaded sRNA rather than the general pool of sRNAs present in a sample of interest. In other words, the invention is directed to a method of isolating only those sRNAs that are loaded onto a RISC at the time of purification i.e. RISC-loaded sRNAs.

The term "Argonaute (AGO)-family protein" herein refers to members of the Argonaute protein family which form the core components of any RISC acting at the RNA or DNA level. AGO proteins are evolutionary conserved among eukaryotes and can be separated into AGO and PIWI sub-families. All AGO/PIWI proteins comprise three key domains: PIWI, PAZ and Mid, and bind different classes of sRNAs which guide them to their specific targets through nucleotide sequence complementarity (base pairing). AGO-bound sRNAs might be functionally inert or might promote mRNA cleavage, enhanced mRNA decay and/or translation inhibition or, alternatively, chromatin compaction and/or altered transcription or, alternatively, physical genome modification/editing. While the complete suite of RISC components is yet to be fully elucidated, AGO proteins have been confirmed as invariable key elements of such complexes. Consequently, the terms "AGO-associated", "AGO-bound", "AGO-loaded", "RISC-associated", "RISC-bound" and "RISC-loaded" are herein used interchangeably.

The terms "associated" or "loaded" herein refers to non-covalent binding of a sRNA molecule to an AGO-family protein.

Like IP-based or AGO-PAPP methods, the principle of the invention is based on the notion that the most useful sRNA information will be contained within functional RISCs, i.e., those sRNAs potentially engaged in gene regulation by guiding an AGO. Isolating AGO-bound sRNAs also concomitantly offers the advantage of significantly eliminating other nucleic acids unrelated to sRNAs. However, unlike IP or AGO-PAPP, the method according to the invention does not isolate RISC-associated sRNAs based on immuno-enrichment or AGO-AGO-hook affinity, but instead by exploiting conserved biochemical properties exhibited by all known AGO/PIWI proteins loaded with sRNA cargoes, including, chiefly, a isoelectric point comprised between 9.3 and 9.8 under physiological conditions.

By contrast, under such conditions, all free nucleic acids are heavily negatively charged. Therefore, it is possible to selectively remove non RISC-associated nucleic acids from a native lysate. For example, the lysate may be exposed to a positively charged resin, so that all contaminating, free nucleic acids (RNA, DNA) remain bound to it and are thus removed from the lysate. Once the resin is washed, mild salt concentrations can be applied to collect RISC-associated sRNAs. Thus, the isolation principle of the method according to the invention is based upon retention as opposed to enrichment (see FIG. 1A).

The invention is directed to the purification of RISC-associated sRNAs from a sample, in particular to the purification of RISC-loaded sRNAs. The sample may be derived from a biological specimen such as cells, biological fluids, biopsies of a tissue, or organ of an animal, fungus, protozoan or plant. In one embodiment, the biological specimen is a whole organ of an animal, fungus, protozoan or plant. Likewise, the sample may be derived from a biological specimen of cell culture of animal, fungus, protozoan or plant cells. In this aspect, the sample may also comprise the supernatant from a cell culture specimen. The specimen may also consist of one or several whole organisms.

In a preferred embodiment, the sample is a biological specimen from a mammal, in particular a specimen derived from a human subject or a human patient. The specimen may be a whole-blood sample, a serum sample, a plasma sample, a cerebro-spinal fluid sample, a saliva sample, a lachrymal fluid sample, a urine sample, a stool sample, a lymph sample, a milk sample, a seminal fluid sample, an ascites or an amniotic fluid sample.

In another embodiment, the animal from which the specimen is derived is any animal of veterinary interest, including, but not restricted to, zoo animals, pets, cattle, poultry and fish. In another embodiment, the animal is a nematode or yeast.

In yet another embodiment, the specimen is a biological fluid from any plant, e.g. xylem or phloem.

Biological specimen may be fresh or frozen-stored as freezing does not modify the biochemical properties required for the application of the method according to the invention.

Biological specimens used to obtain the native samples according to the invention may be treated in order to facilitate purification of sRNAs prior to use as samples in the method of the invention. For example, the specimen may be washed with standard buffers (PBS for cell culture, M9 buffer for nematodes or sterile physiological water for biopsies derived from animals). Once the washing buffer is removed, dry pellets may be flash frozen in liquid nitrogen or dry ice and may be used as samples according to the invention.

Collected cells may be separated using suitable standard procedures. The skilled person knows how to select a suitable procedure for separating different cells in a specimen. Suitable methods may be Ficoll-Plaque® (GE Healthcare, 17-1440-02), Lymphoprep™ (STEMCELL Technologies, 07801) or fluorescence activated cell sorting (FACS). After sorting, cells may be pelleted by centrifugation. Once the washing buffer is removed from the pelleted cells, dry pellets may be flash frozen in liquid nitrogen or dry ice and may be used as samples according to the invention.

According to the invention, a biological fluid may be collected and subsequently flash frozen in liquid nitrogen or dry ice. Collected samples may be stored frozen, preferably at −80° C. The skilled person is aware that freezing/defrosting cycles should be minimized to preserve the quality of the material. In a preferred embodiment, aliquots of specimens are prepared prior to freezing, e.g. 2.5 million cells, 10 *Drosophila* ovary pairs, 20 mg of plant/animal material, 50 to 100 μL whole nematode or fungi pellets, 150 μL bio fluid.

In one embodiment of the invention, the biological specimen is a RISC-containing sample generated by in vitro, in cellulo or in vivo RISC production.

As used herein, the term "lysis" refers to destabilization, using detergents, of the cytoplasmic membranes, vesicles, organelles and nuclear envelopes of the sample, in order to access to their proteins content. The term "native lysis" refers to a lysis performed using detergents with low stringency at optimized concentration in order to retain the protein-protein interactions (protein complexes), RNA-protein interaction (ribonucleoprotein) and their enzymatic activity.

The skilled person is aware that the different buffers used for lysis and elution in any purification method should be compatible with each other. Consequently, the different buffers used in some embodiments of the invention are based on the same basic buffer and differ from each other only by the addition of specific compounds or adjustment of other properties, such as preserving agents, detergents or salt concentration necessary for the desired purpose (i.e., column storage, lysis, elution).

The buffers used in these embodiments are optimized to (i) solubilize RISCs while preserving the non-covalent interaction between sRNAs and AGO proteins, (ii) favor retention of all other nucleic acids on the positively charged matrix and (iii) allow AGO-bound sRNA separation based on differences in isoelectric point. These combined biochemical properties are obtained using specific salt concentrations which were surprisingly found by the inventors. In a preferred embodiment, potassium acetate ($CH_3CO_2K$) is used as the salt.

The specific salt concentrations in the different buffers used in the embodiments of the invention are monitored by conductivity measurements. The term "conductivity" herein refers to the ability of an electrolyte solution to conduct electricity. Conductivity measurement is a fast, inexpensive and reliable way to measure the ionic content (salt concentration) of a solution routinely used in industrial processes. The international unit for conductivity is Siemens per meter (S/m). The $CH_3CO_2K$ concentration of the buffers used in these embodiments are adjusted by monitoring the buffer conductivity until specific values are reached.

In a preferred embodiment, the basic buffer consists of 20 mM HEPES-KOH adjusted to pH=7.9 to allow better pH stability over a range of temperatures; 10 to 20% (v/v) glycerol to preserve AGO-sRNA interactions; reducing agents such as 1 mM dithiothreitol (DTT) to prevent oxidization; and 0.2 mM EDTA to chelate divalent cations before addition of excess $Mg^{2+}$ with 1.5 mM MgCl2.

In a preferred embodiment, the basic buffer is complemented with 2 mM $NaN_3$ as a preserving agent and 100 mM $CH_3CO_2K$ final to obtain the storage buffer (measured conductivity comprised between 7.5 and 8.5 mS/cm$^2$). This buffer ensures optimal resin storage within the column.

In a preferred embodiment, the basic buffer is complemented with 0.1% (v/v) TRITON-X100 as zwitterionic detergent to solubilize the RISC content in basic buffer at 100 mM $CH_3CO_2K$ final used for lysis (measured conductivity comprised between 7.5 and 8.5 mS/cm$^2$).

In a preferred embodiment, buffers used in the invention are filtered at 0.22 μm and degassed. The buffers may further be validated by conductivity measurement and/or benchmarked sRNAs isolation. The buffers may further comprise additional, commercially available compounds suitable for protein and RNA stabilization.

According to the invention, the samples may be solid or liquid. Solid samples are mechanically transformed into powder using standard procedures adapted to the respective biological model, then homogenized in lysis buffer. Liquid samples are mixed with lysis buffer at a ratio of 1:1 (v/v). Lysis disrupts cell wall, membranes and the nuclear envelope, leading to subsequent RISCs solubilization. The skilled person is well aware of the properties of various lysing agents and of how to select an appropriate amount of lysing agent. In addition, the skilled person knows how to measure the effect of a lysing agent onto a given biochemical interaction, a given resin, using given salts and at a given pH.

Since the method of the invention aims at obtaining native state RISCs, the lysis buffer may not contain chaotropic agents such as guanidium salts or urea at concentrations that would dissociate the sRNA from the complex. In a preferred embodiment, the lysis buffer contains between 0.05% (v/v) and 0.2% (v/v) Triton X-100, preferably between 0.1% (v/v) and 0.2% (v/v) Triton X-100, most preferably 0.1% (v/v) Triton-X-100. The lysis buffer may additionally contain a zwitterionic detergent, such as 3-[(3-cholamidopropyl) dimethylammonio]-1-propanesulfonate (CHAPS), and may be supplemented with an RNase inhibitor and/or a protease inhibitor.

The lysis buffer comprises or consists of 20 mM HEPES-KOH (pH 7.9), 10 to 20% (v:v) glycerol, 1.5 mM $MgCl_2$, 0.2 mM EDTA, 1 mM DTT and 100 mM $CH_3CO_2K$ and 0.1% Triton X-100, with a measured conductivity from 7.5 to 8.5 mS/cm$^2$. In a preferred embodiment, the lysis buffer have a measured conductivity of 8 mS/cm$^2$.

In one embodiment, the lysate thus obtained can be directly used for subsequent steps, thereby facilitating handling of the sample.

In another embodiment, the native lysate is clarified from insoluble material once RISCs are solubilized in lysis buffer according to the invention. Such clarifying can be carried out through e.g. sedimentation, filtration or by a short centrifugation. Herein, the terms "spin" and "centrifugation" are used interchangeably.

In one embodiment, a centrifugation at 10 000×g, 4° C., 5 minutes is applied to the sample in order to remove insoluble material, such as, e.g., membrane debris or plant cell walls. The supernatant is transferred into a fresh tube, and constitutes the clarified lysate ready for purification of functional sRNAs according to the invention.

In another embodiment, the native lysate is clarified by filtration. For example, filtration is carried out by applying the lysate to a filtration column that retains insoluble material such as membrane debris or plant cell walls, but lets the solubilized RISCs pass through. Filtration can be carried out using centrifugation or by applying a vacuum to the lysate loaded filtration column. In a preferred embodiment the lysate is loaded onto a centrifugation column with a 0.45 μm cellulose acetate filter such as Costar Spin-X (Corning, Cat-No: CLS8162) and centrifugated for 5000×g, 4° C. for 2 minutes.

In yet another embodiment, the filtration membrane is included on top of the anion exchange resin in the column containing the resin, providing a first filtration compartment where the native lysate is added and filtered and a second compartment containing the anion exchange resin, thereby seamlessly integrating the clarifying filtration and the loading of the anion exchange resin. In a preferred embodiment the first filtration compartment is provided as a removable insert.

Clarifying the lysate offers the advantage that cell debris that could clog the column and otherwise hinder enrichment of the RISC-associated sRNAs are removed.

According to one embodiment of the invention, RISC-associated sRNAs are eluted from the column when an elution buffer is added to the column. The elution buffer differs from the lysis buffer by the absence of a detergent and by a higher salt concentration, validated by conductivity measurement. The elution buffer comprises or consists of 20 mM HEPES-KOH (pH 7.9), 10 to 20% (v/v) glycerol, 1.5 mM $MgCl_2$, 0.2 mM EDTA, 1 mM DTT and a $CH_3CO_2K$ concentration comprised between 400 and 800 mM, to reach a measured conductivity comprised between 30 and 50 $mS/cm^2$. In a preferred embodiment, the elution buffer have a measured conductivity of 40 $mS/cm^2$.

The column according to one embodiment of the invention comprises a column body and an resin. The column body may have any suitable shape and volume. The volume of the column body depends on the desired application and may be between 50 μl and 50 L, preferably between 100 μl and 1000 μl, particularly preferably between 200 μl and 800 μl. In one embodiment, the column body may have a volume of 50 μl, 100 μl, 150 μl, 200 μl, 250 μl, 300 μl, 350 μl, 400 μl, 450 μl, 500 μl, 550 μl, 600 μl, 650 μl, 700 μl, 750 μl, 800 μl, 900 μl, 1000 μl. In a preferred embodiment, the volume of the column body is 1000 μl. In another preferred embodiment, the volume of the column body is 200 μl. A low volume of the column body allows working with minimal amounts of material. According to the invention, the column body is suitable for centrifuging the clarified sample and elution buffer in a 2 mL microcentrifuge tube in order to streamline the procedure. Typically, the column body is made of a 1000 μL polypropylene tube, but any other material showing similar properties may be used. In a preferred embodiment, Microspin™ columns (GE healthcare, GE27-35-650, REF 27356501) are used as column bodies.

In one embodiment, the column body is a 96 well plate. This allows using the method according to the invention for automated high throughput analysis. In another embodiment, the column is a microfluidic chip that also allows the automatization of the purification procedure.

According to one embodiment of the invention, the column body comprises an anion exchange resin stored, preferably in a storage buffer, i.e. the column body is packed with said resin. Any anion exchange resin may be used for the invention, as long as the system preserves the non-covalent interaction between sRNAs and AGO proteins, while allowing separation of all other AGO-free nucleic acids on the positively charged matrix to proceed with the separation. The skilled person knows how to choose a suitable anion exchange resin to allow for sRNA purification using different buffers, different salts and at different pH values. In a preferred embodiment, Q Sepharose HP resin (GE healthcare GE17-5072-01), is used as anion exchange resin in the method of the invention.

Before packing the anion exchange resin into the column body, the anion exchange resin may be equilibrated. In a preferred embodiment, the anion exchange resin is equilibrated in equilibration buffer comprising 20 mM HEPES-KOH (pH 7.9), 10 to 20% (v/v) glycerol, 1.5 mM $MgCl_2$, 0.2 mM EDTA, 1 mM DTT and 100 mM $CH_3CO_2K$, with a measured conductivity of 8 $mS\cdot cm^2$. This influences the anion exchange resin's separation properties. According to the invention, the anion exchange resin may be washed 1, 2, 3, 4 or 5 times prior to packing the column, then re-suspended in a suitable volume of storage buffer and packed into the column body. In a preferred embodiment, the complete volume of the column body is packed with the anion exchange resin in order to maximize the column's separation property for a given elution volume. Typically, this consists in 800 μL of storage buffer/resin in ratio of 3:5 in GE Microspin™ columns.

In another embodiment, the column body is only partially packed with the anion exchange resin in order to lower costs, considering that a lower column capacity can suffice for further sRNA analysis since the amount of sample may be decreased in proportion to the amount of resin. In another embodiment, the column body size and the volume of packed resin is decreased in order to allow sRNA purification from minute amount of samples, (e.g., 5000 *Arabidopsis* embryonic cells or up to one *Arabidopsis* flower bud).

Columns and buffers used in the invention are prepared in batches in advance, with each batch being validated by conductivity measurement and molecular assays, and subsequently stored at 4° C. The storage buffer, according to the invention, may additionally comprise compounds preventing microbial contamination, e.g., sodium azide ($NaN_3$).

In a preferred embodiment, the elution step of the method of the invention is repeated for a second time. This ensures that all RISC-associated sRNAs are washed off the column, resulting in a higher yield of RISC-associated sRNAs. In another embodiment of the invention, the elution step may be performed by applying a gradient of increasing salt concentration.

The method according to the invention enables robust and consistent purification of AGO-associated sRNAs in the most complex organisms, the most recalcitrant tissues and/or from the most limiting amounts of starting biological material.

The kit according to the invention is conditioned, shipped and operational at room temperature, and overcomes the main caveats of other state-of-the-art methods by providing a highly simplified, universal and single-step anion-exchange purification procedure for RISC-associated sRNAs.

The method according to the invention can be run within 15 minutes on the bench with bare minimal laboratory requirements, thus greatly reducing work time and costs.

The method according to the invention is fully suitable for sRNA isolation from notoriously difficult-to-handle tissues including starchy plant storage roots or Heparin/EDTA-treated mammalian blood samples.

RISC-associated sRNAs isolated according to the invention are not affected by harsh conditions in the sample leading to global RNA degradation in the sample. In addition, RISC-associated sRNAs isolated according to the invention are immediately suitable for northern analysis, quantitative RT-PCR and microarray analysis, as well as deep-seq using any in-house or commercial cloning protocols, and all state-of-the-art sequencing platforms. By restricting the analysis to AGO-bound sRNAs, the invention allows a higher multiplexing of the sRNAs libraries prior to deep-seq, thereby significantly reducing costs of downstream analyses.

RISC-associated sRNAs isolated according to the invention are also particularly resilient to degradation and may be frozen after isolation.

The method according to the invention typically achieves >95% enrichment of the desired sRNA species over contaminating/degraded RNAs, thus providing unprecedented quality of the isolated sRNA.

The method according to the invention allows sRNA deep-seq with a yield, purity and quality at least on par with that achieved by gold standard size selection on gel, both in plants and animals. The method of the invention does not exhibit sequencing biases based on endo-siRNA and miRNA correlation analyses in either organisms.

In a preferred embodiment, the method of the invention is combined with the NEBnext® smallRNA library Prep kit (NEB, Ipswich, MA, Catalog #E7330), allowing truly direct sRNA cloning bypassing altogether the step of post-PCR size selection of the library.

The RISC-associated sRNA fraction obtained when performing the method of the invention may be adapted to a downstream silicate-based separation procedure using commercially available columns to bypass the need for RNA precipitation altogether, thus allowing direct access to purified sRNAs in less than 30 minutes. Following RISCs purification, in one embodiment of the invention, a deprotenization step using phenol/chloroform/isoamylic alcohol is performed, followed by isopropanol-based precipitation to allow sRNA recovery, in order to remove the protein content from the collected RISCs. This step, however, requires long incubation at low temperature followed by centrifugation at high speed which is technically challenging and time consuming.

Although nucleic precipitation is a cost effective and high output standard procedure, commercially available silicate columns can be used to directly isolate sRNAs after deprotenization. In one embodiment of the invention, the method entails fixation of sRNAs after removal of the protein content to a column matrix in the presence of alcohol, thereby relying on hydrophobic interaction. The sRNAs may then be washed from impurities and finally eluted in water. In a preferred embodiment, ZYMO microspin IC columns (Zymo Research, Freiburg, Germany, REF C1004-50) are used according to the manufacturer's instruction. The inventors have surprisingly found that the sRNA output versus elution volume are optimal compared to similar commercially available systems, thus allowing for subsequent sequencing.

The inventions also relates to a kit for the purification of AGO-associated sRNA, comprising a) a lysis buffer;

b) an elution buffer; and c) a column comprising an anion exchange resin.

The kit according to the invention may comprise buffers as described above.

The present invention may be used for the diagnosis of diseases or subtypes of diseases associated with the presence of particular sRNAs. For example, in human, increased levels of the Let-7 miRNA are nearly always positively correlated with lung cancer, while miR-21 levels are usually increased in glioblastoma and breast cancer. miR-15a/16a is frequently absent or strongly reduced in B-cells leukemia while miR-155 is increased in B-lymphoma and breast cancer. miRNA profiling may also be used to refine the state or the complex composition of tumors in biopsies, and may also help determining the tissues from which a tumor might originate during metastasis or in case of undifferentiated tumors. All these miRNA-based readouts hold great promises in terms of profiling cancers and their origins, effectively granting much more personalized and targeted disease treatment. The potential use of miRNAs as biomarkers is not restricted to cancer and may apply to any condition in which cellular homeostasis is perturbed by say, a metabolic or genetic dysfunction, or an infection. For instance, elevated miR-122 in hepatocytes is usually a sign of liver dysfunction and/or hepatitis virus infection. Examples of the few circulating miRNAs already being used as biomarkers include miR-14 in the plasma, whose abundance has become a major criterion for the unambiguous and non-invasive diagnostic of prostate cancer; high plasma levels of miR-141 are associated with poor prognosis in colorectal cancer. Several other circulating, plasma miRNAs have been correlated with cardiovascular diseases, organ dysfunctions (kidney/miR-215, liver/miR-122, pancreas/miR-375) or even complicated gestation due to trophoblast/placental defects.

Consequently, the invention also relates to a method to identify sRNAs as biomarkers of a pathological state, to diagnose such pathological state and ultimately to provide information on its possible evolution (prognosis). Given that the method of the invention yields highly pure AGO-associated sRNAs even from notoriously recalcitrant specimen, such as plasma, it can be used for identification of circulatory biomarkers. This implies access to plasma samples from a cohort of healthy individuals comparable in gender and age to a cohort of patients. The method according to the invention may be used to purify plasma-borne AGO-associated sRNAs to be then subjected to deep-seq. The resulting datasets, corresponding to circulating sRNA populations of each individual may subsequently be analyzed in order to determine significant differences in term of identity or abundance (up- or down-regulation) of a particular set of sRNAs in patients versus healthy individuals. The relevance of such markers for diagnosis/prognosis may be then validated on an independent set of patients. Once a set of sRNAs identified as biomarkers is validated, the method of the invention may be coupled to targeted quantification via qRT-PCR in patients. The inventors, in collaboration with clinicians, have already obtained preliminary results demonstrating how the method according to the invention can be used reliably to identify patients afflicted by a rare auto-inflammatory disease.

Embodiments (1) A method for the purification of RISC-associated sRNAs, comprising the following steps:

a) providing a native sample derived from a biological specimen;

b) lysing the sample using a native lysis buffer;

c) selectively removing non RISC-associated nucleic acids from the lysate; and d) collecting RISCs comprising RISC-associated sRNAs.

(2) A method according to embodiment (1), wherein in step c), non-RISC associated nucleic acids are removed from the lysate by loading the lysate onto a column comprising a resin allowing the fixation of nucleic acids.

(3) A method according to embodiment (1) or (2), wherein the lysis buffer comprises or consists of 20 mM HEPES-KOH (pH 7.9), 10 to 20% (v:v) glycerol, 1.5 mM $MgCl_2$, 0.2 mM EDTA, 1 mM DTT and 100 mM $CH_3CO_2K$ and 0.1% Triton X-100, with a measured conductivity from 7.5 to 8.5 mS/$cm^2$.

(4) A method according to embodiment (1) or (2), wherein in step d) RISCs are collected by applying an elution buffer to the column.

(5) A method according to embodiment (3), wherein the elution buffer comprises or consists of 20 mM HEPES-KOH (pH 7.9), 10 to 20% (v/v) glycerol, 1.5 mM $MgCl_2$, 0.2 mM EDTA, 1 mM DTT and a $CH_3CO_2K$ concentration comprised between 400 and 800 mM, to reach a measured conductivity comprised between 30 and 50 mS/$cm^2$.

(6) A method according to any of the embodiments, wherein the resin is an anion exchange resin.

(7) A method according to any of the embodiments, wherein in step b) the lysate is clarified by a short centrifugation or by filtration.

(8) A method according to any of the embodiments, wherein the column is a 96 well plate or a microfluidic chip.

(9) A method according to any of the embodiments, wherein the specimen is from a human.

(10) A method according to any of the embodiments, wherein the biological specimen is a RISC-containing sample generated by in vitro, in cellulo or in vivo RISC production.

(11) A method according to any of the embodiments, further comprising:

e) removing the protein content from the collected RISCs using phenol/chloroform/isoamyl-alcohol extraction; or f) removing the protein content from the collected RISCs using proteinase K treatment.

(12) A method according to any of the embodiments for use in the diagnosis of a disease whose diagnosis or prognosis is characterized by the presence of particular sRNAs.

(13) A method for use according embodiment (10), wherein the disease is a cancer, a metabolic disorder, an hereditary condition or an infectious disease.

(14) A kit for the purification of RISC-associated sRNAs, comprising:

a native lysis buffer;

an elution buffer; and a column comprising an anion exchange resin stored in storage buffer.

(15) A kit according to embodiment (12), wherein the lysis buffer comprises 20 mM HEPES-KOH (pH 7.9), 10 to 20% (v/v) glycerol, 1.5 mM $MgCl_2$, 0.2 mM EDTA, 1 mM DTT, 100 mM $CH_3CO_2K$ and 0.1% Triton X-100, with a measured conductivity from 7.5 to 8.5 mS/$cm^2$.

(16) A kit according to embodiments (12) or (13), wherein the elution buffer comprises 20 mM HEPES-KOH (pH 7.9), 10 to 20% (v/v) glycerol, 1.5 mM $MgCl_2$, 0.2 mM EDTA, 1 mM DTT and a $CH_3CO_2K$ concentration comprised between 400 and 800 mM, to reach a measured conductivity comprised between 30 and 50 mS/$cm^2$.

(17) A kit according to embodiments (12) to (14), wherein the storage buffer comprises 20 mM HEPES-KOH (pH 7.9), 10 to 20% (v/v) glycerol, 1.5 mM $MgCl_2$, 0.2 mM EDTA, 1 mM DTT, 100 mM $CH_3CO_2K$, with a measured conductivity from 7.5 to 8.5 mS/$cm^2$, and 2 mM $NaN_3$.

EXAMPLES

Example 1

Principle of the Method According to the Invention

The scheme presented in FIG. 1A depicts the principle of the method according to the invention. A native lysate is produced from the biological sample in a manner so as to preserve non-covalent interactions between AGO proteins and associated sRNAs. The lysate is mixed with a positively charged resin allowing the fixation of the non-AGO-loaded nucleic acids onto the resin whereas RISCs, which are not fixed, can be eluted. The separation procedure, based on the charge difference between RISC-associated RNAs and other cellular nucleic acids, generates a RISCs-enriched fraction (called E fraction). To control the procedure, the retained free nucleic acids can be eluted in a distinct fraction (referred to as HS fraction) using a high salt buffer.

Detailed Procedure for the Use of Mini-TraPR Kit

As depicted in the scheme presented in FIG. 1B, the procedure entails three main steps. The sample is lysed in the native lysis buffer and clarified by a quick centrifugation. The clarified lysate is then loaded onto a column body containing the positively charged resin. The lysate and the resin are mixed to favour the separation, then the column is centrifuged and the flow through is collected in a fresh tube. An elution step is then performed by adding elution buffer to the column followed by a short centrifugation. The eluate is collected in the previous tube. The elution is repeated one more time to ensure a complete recovery of the RISCs. Following this procedure, the RISCs content of the sample is purified in 15 minutes, upon which AGO-associated sRNAs can be extracted from the collected fraction.

Buffers

Resin equilibration buffer (20 mM HEPES-KOH pH=7.9, 10% (v/v) glycerol, 1.5 mM $MgCl_2$, 0.2 mM EDTA, 1 mM DTT, conductivity adjusted at 8 $mS \cdot cm^{-2}$ with potassium acetate at an indicative concentration of ~0.1M))

Resine storage buffer (20 mM HEPES-KOH pH=7.9, 10% (v/v) glycerol, 1.5 mM $MgCl_2$, 0.2 mM EDTA, 1 mM DTT, 0.2 mM sodium azide, conductivity adjusted at 8 $mS \cdot cm^{-2}$ with potassium acetate (KoAc) at an indicative concentration of ~0.1M)

TraPR Lysis buffer (20 mM HEPES-KOH pH=7.9, 10% (v/v) glycerol, 1.5 mM $MgCl_2$, 0.2 mM EDTA, 1 mM DTT, 0.1% (v/v) Triton X100, conductivity adjusted at 8 $mS \cdot cm^{-2}$ with KoAc at an indicative concentration of ~0.1M)

TraPR Elution buffer (20 mM HEPES-KOH pH=7.9, 10% (v/v) glycerol, 1.5 mM $MgCl_2$, 0.2 mM EDTA, 1 mM DTT, conductivity adjusted at 40 $mS \cdot cm^{-2}$ with KoAc at an indicative concentration of ~0.44M)

TraPR High Salt buffer (20 mM HEPES-KOH pH=7.9, 10% (v/v) glycerol, 1.5 mM $MgCl_2$, 0.2 mM EDTA, 1 mM DTT, conductivity of the HS buffer is adjusted at 110 $mS \cdot cm^{-2}$ with KoAc at the indicative concentration of ~4M)

1. Sample Lysis and Clarification

Lyse flash frozen samples in 400 μL TraPR Lysis buffer (nitrogen precooled mortar, dounce, or others method);

Transfer lysate into a fresh DNase, RNAse free 1.5 mL microcentrifuge tube;

Clarify lysate is by centrifugation at 10 000×g, 5 minutes, 4° C.;

Transfer 300 μL of clarified lysate into a fresh DNase-, RNAse-free 2 mL microcentrifuge tube;

2. Mini TraPR Kit Column Preparation

Re-suspend the resin in the column by vortex few second;

Loosen the cap one quarter turn and twist off the bottom closure (do not trash the bottom closure);

Place the column in a 2 mL microcentifuge tube;

Centrifuge 15 seconds on bench microcentrifuge;

Discard the collection tube, and place the column on fresh 2 mL microcentrifuge tube labeled "TraPR E fraction"

3. Sample Application

Close the column with the bottom closure;

Open the column cap, apply 300 μL of sample to the top center of the resin;

Close column cap and mix sample and resin by inverting vigorously;

Remove the bottom closure, and place the column into previous 2 mL microcentrifuge tube labeled "TraPR E fraction"

4. Elution of RISC Loaded SmallRNAs

Centrifuge 15 seconds on bench microcentrifuge, save flowthrough;

Open the column cap, apply 300 μL of TraPR Elution Buffer;

Close the column and place into previous 2 mL microcentrifuge tube labeled "TraPR E fraction";

Centrifuge 15 seconds on bench microcentrifuge;

Repeat step 15 to 17 once, collect eluate in the same 2 mL microcentrifuge tube labeled "TraPR E fraction";

Close the "TraPR E fraction" collection tube (900 μL) at store on ice for immediate use, or store at −80° C. This fraction contains the RISCs proteins (AGOs) loaded with their cognate sRNAs.

5. RNA Extraction (Precipitation)

Add 500 μL acidic PCI to the fraction collected;

Vortex vigorously;

Centrifuge 5 min, full speed, 4° C.;

Collect the aqueous phase in new 1.5 mL microcentrifuge tube;

Add 10% of NaAcetate 3M, pH 5.2 and 1 μL Glycogen, homogenize;

Add 120% cold isopropanol, homogenize;

Incubate at least 30 min at −20° C.;

Centrifuge 30 min, full speed, 4° C.;

Discard liquid phase;

Add 400 μL cold 80% ethanol;

Centrifuge 5 min, full speed, 4° C.;

Repeat steps 29 to 30 two more time;

Remove all ethanol;

Add adapted volume of water (or LMNb loading buffer 1×) to the pellet;

Resuspend by pipetting up and down (can be heated few minutes at 60° C.);

RNA can be stored at −80° C., or immediately used.

6. RNA Extraction (Zymo Ic Microspin Silicate Column)

Add 500 μL acidic PCI to the fractions collected;

Vortex vigorously;

Centrifuge 5 min, full speed, 4° C.;

Collect the aqueous phase in 2 new 1.5 mL microcentrifuge tubes (split the collected phase in 2 equal volumes);

Add 2 volumes of RNA MAX buffer in each tubes and mix well;

Transfer 800 μL of the mixture in Ic column, placed into a collection tube;

Centrifuge 30 sec., 12 000 g, discard the flow through;

Repeat steps 41 and 42 until all the mixture is passed through the column;

Add 400 μRNA Prep buffer to the column;

Centrifuge 1 min., 12 000 g, discard the flow through;

Add 800 μL RNA Prep buffer to the column;

Centrifuge 30 sec., 12 000 g, discard the flow through;

Repeat steps 46 and 47 with 400 μL RNA Prep buffer;

Centrifuge 2 min, 12 000 g the column to completely remove the buffer;

Transfer the column on a new 1.5 mL microcentrifuge tube;

Add 6 to 15 μL of water pre warmed at 60° C. on the resin;

Incubate at room temperature for 1 minute;

Centrifuge 1 min., 10 000 g to elute RNA;

Recovered RNA can be used immediately, or stored at −80° C.

Example 2

*Arabidopsis* AGOs and Their Associated sRNAs Co-Purify in the RISCs-Enriched E Fraction According to the Method of the Invention The *Arabidopsis thaliana* genome encodes 10 paralogous AGO genes of which 9 are expressed as proteins classified into 3 major phylogenetic clades, as depicted in FIG. 2A. Immunoblot analysis of two major AGO proteins (AGO1 and AGO4) from *Arabidopsis* inflorescences subjected to elution from the column obtained by applying buffer with increasing concentration of salt, of which the conductivity was monitored (FIG. 2B, top). The RNAs contained in the fractions were extracted and subjected to migration on 17% acrylamide gel, then stained with ethidium bromide (FIG. 2B, bottom). Analysis of the elution profile reveals that the two main *Arabidopsis* AGO proteins are eluted from the column before mild salt concentration buffer is applied (black arrow), as opposed to RNAs that are retained on the resin until higher salt concentration are reached (dashed arrow). The result presented in FIG. 2B have been used to define a range of salt concentration in the elution buffer (monitored by a conductivity comprised between 30 and 50 mS/cm$^2$) that allow the separation of AGO proteins from cellular nucleic acids such as long RNAs.

To extend this analysis to the entire *Arabidopsis* AGO protein family (nine members), protein analysis by immunoblot was conducted using antibodies to detect 7 endogenous AGO proteins following RISC purification form *Arabidopsis,* using an elution buffer adjusted to 40 mS/cm$^2$ according to the method of the invention (FIG. 2C). To demonstrate the specificity of the antibodies, individual *Arabidopsis ago* mutant lines were analysed side-by-side to wild type plants (left of the gel). After purification according to the method of the invention, all 7 AGOs detectable in inflorescences were recovered and enriched in the E fraction, with no overt signal in the HS fraction (right part of the gel). As there are no available antibodies recognizing native AGO3 and AGO7, the same experiment was conducted using transgenic lines expressing epitope-tagged versions of each protein under their endogenous promoter. RISCs were then extracted from tissues known to express those specific AGOs, i.e. young siliques and seedlings for AGO3 and AGO7, respectively. As shown in FIG. 2D, AGO3 is enriched in the E fraction and below detection in the HS fraction. A similar result is observed for AGO7 in FIG. 2E. The results demonstrate that RISC purification according to the method of the invention enables a strong enrichment of all expressed *Arabidopsis* AGO proteins in the E fraction.

Deep-seq analyses shows that total plant sRNAs are constituted of two major species of diagnostic, discrete length: highly abundant, 24-nt heterochromatic siRNAs derived from transposons and repeats are loaded into AGO4-clade AGOs whereas abundant 21-nt sRNAs are composed of mostly miRNAs loaded into AGO1-clade AGOs and of sRNAs loaded into AGO2. To test the purity of sRNAs purified according to the method of the invention, all fractions (I, E and HS) were subjected to 5'-end labelling with polynucleotide kinase (PNK). FIG. 2F shows that the 21-nt and 24-nt sRNA species are below detection in the I and HS fractions, displaying instead strong labelling of heterogenous and unrelated RNA species. By contrast, both species appear as crisp bands devoid of virtually any background in the AGOs-enriched E fraction, showing the potency of the procedure according to the method of the invention for RISCs purification. The extent of purification seen by 5' labelling is at least on par with that usually observed with highly specific immunoprecipitation. To verify the isolation of specific sRNA species, the RNA contained in each fraction was subjected to northern analysis involving specific radiolabeled oligonucleotide probes for known, representative *Arabidopsis* sRNA species. As shown in FIG. 2G, a strong enrichment is observed for specific species of both the 21-nt and 24-nt sRNA classes in the E fraction. By contrast the non RISC-associated U6 RNA is enriched in the HS fraction as expected.

Figure 2:
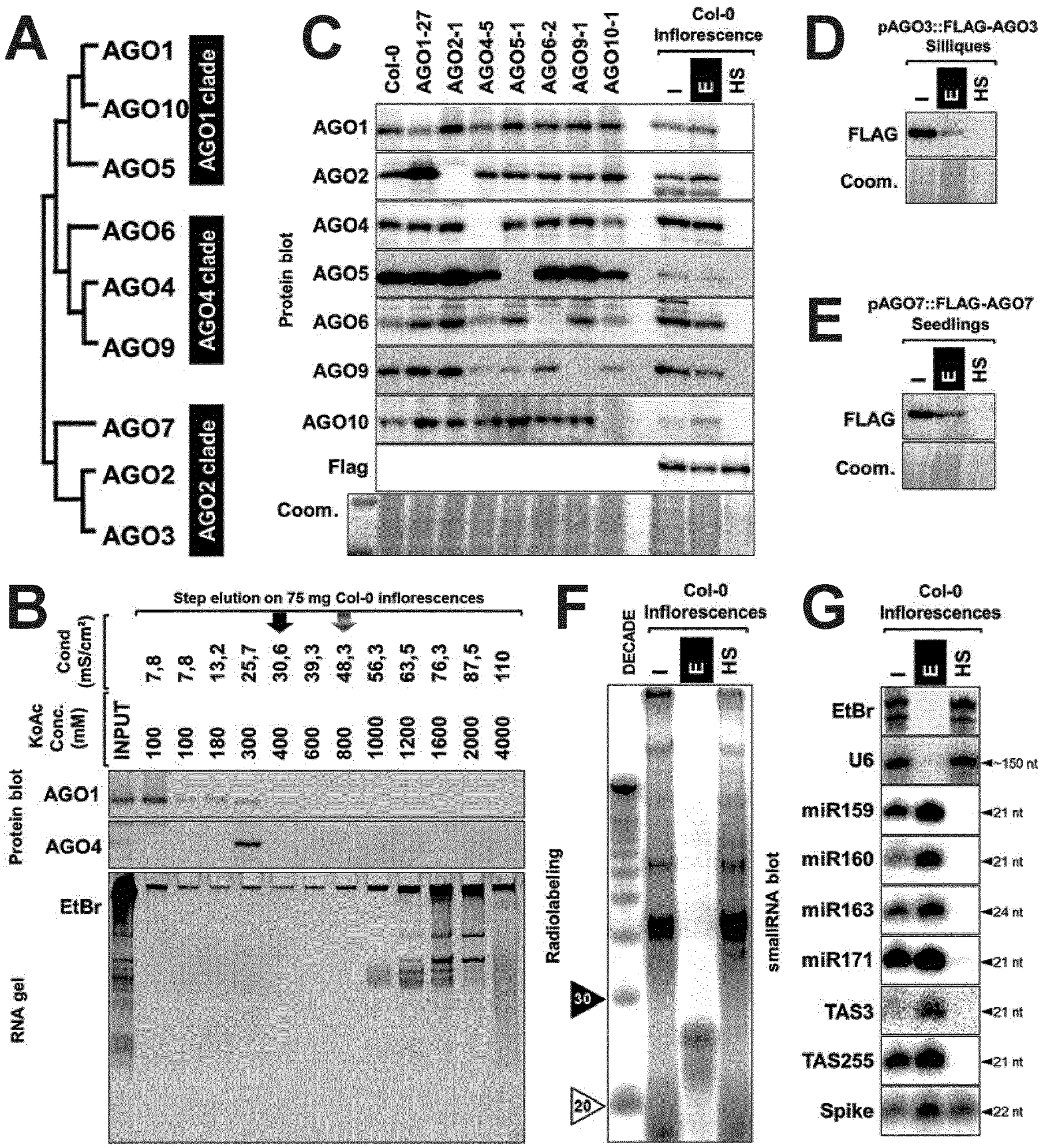
FIG. 2A shows a schematic representation of the phylogeny of the nine AGO proteins expressed in *Arabidopsis thaliana* encompassing three major clades.
FIG. 2B shows a protein blot (top) analysis for the 2 main AGO proteins (AGO1 and AGO4) in *Arabidopsis* inflorescences extracted according to the method of the invention, fractionated using steps of increasing potassium acetate (KoAc) concentration, and detected with antibodies directed against the endogenous proteins. RNAs present in each fraction was extracted, subjected to migration on a 17% denaturing polyacrylamide gel, and detected after ethidium bromide staining (bottom). For each elution step, the conductivity of the buffer (Cond, mS/cm$^2$) was measured. The black arrow indicates the fraction where the cellular AGOs content is eluted, the dashed arrow indicates the maximal salt concentration in the buffer allowing the retention of long RNAs on the resin.
FIG. 2C shows a protein blot analysis for the major AGO proteins in *Arabidopsis* inflorescences sample extracted according to the method of the invention, and detected with antibodies directed against the endogenous proteins (right lanes). The antibodies' specificity is confirmed by comparative analysis of total lysates isolated from individual *Arabidopsis ago* mutants versus wild type plants (Col-0) on the left side of the gel. (I: clarified lysate, E: RISCs fraction, HS: High salt wash of the resin after AGOs elution). "Flag" is a protein spike added in each fraction post-purification as a control for the protein extraction step.
FIG. 2D shows a protein blot analysis of *Arabidopsis* Flag-AGO3 expressed under the AGO3 endogenous promoter extracted from siliques (1-5 days after pollination) according to the method of the invention and detected with an anti-Flag antibody (I: clarified lysate, E: RISCs fraction, HS: High salt wash of the resin after AGOs elution).
FIG. 2E shows a protein blot analysis of *Arabidopsis* Flag-AGO7 expressed under the AGO7 endogenous promoter extracted from 2 week-old seedlings according to the method of the invention and detected with an anti-Flag antibody (I: clarified lysate, E: RISCs fraction, HS: High salt wash of the resin after AGOs elution).
FIG. 2F shows an RNA blot analysis, on a 17% denaturing polyacrylamide gel, of *Arabidopsis* inflorescence RISCs-associated sRNAs extracted according to the method of the invention. RNA purified from the extracted fractions was radiolabeled using T4 PolyNucleotide Kinase (PNK) prior to gel migration and transfer onto a nylon membrane (I: clarified lysate, E: RISCs fraction, HS: High salt wash of the resin after AGOs elution). Ambion® DECADE™ was used as RNA size ladder (nucleotides).
FIG. 2G shows a Low Molecular Weight RNA analysis, on a 17% denaturing polyacrylamide gel, of *Arabidopsis* inflorescence RISCs-associated sRNAs extracted according to the method of the invention. RNA purified from the extracted was separated on gel prior to transfer onto a nylon membrane. Radiolabeled oligonucleotides were used as probes to reveal specific, known *Arabidopsis* sRNAs species as indicated on the right hand side (I: clarified lysate, E: RISCs fraction, HS: High salt wash of the resin after AGOs elution). Spike is a synthetic 22-nt RNA sequence added in each fraction post-purification as a control for the RNA extraction step.

The results presented in FIG. 2 are representative of the pattern routinely obtained in the laboratory by applying the purification according to the method of the invention to *Arabidopsis* lysates from various tissues. They confirm that the procedure allows co-elution of *Arabidopsis* AGO proteins with their sRNAs cargos and efficiently separates most contaminating RNA and breakdown products thereof, which elute, instead, in the HS fraction.

Figure 3:
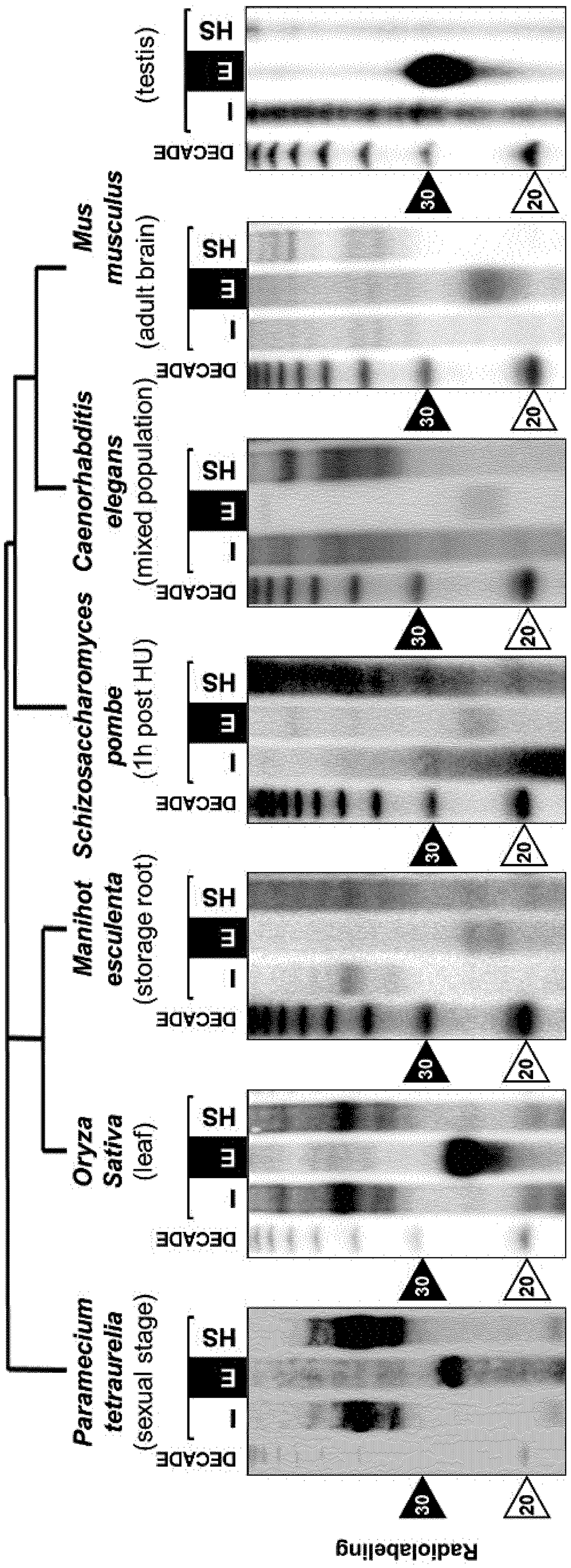
FIG. 3 shows an RNA blot analysis, on a 17% denaturing polyacrylamide gel with RISCs extracted from various organisms as indicated. (I: clarified lysate, E: RISCs fraction, HS: High salt wash of the resin after AGOs elution). Ambion® DECADE™ was used as a RNA size ladder (nucleotides).

The Method of the Invention Defines a Universal RISCs Purification Procedure in a Broad Range of Organisms Given that AGO proteins and their interaction with sRNAs to form RISCs is a highly conserved feature in all kingdoms of life, the purification procedure according to the method of the invention was tested in a range of organisms. The schematic phylogenetic tree presented in FIG. 3 (top) gives an overview of the diversity of organism tested, from ciliates, crops, fission yeast, worms to mammals. For each organism, RISCs were purified according to the method of the invention and their cargoes tested by PNK radiolabelling of the RNAs present in each fractions I, E and HS, as shown in FIG. 3 (bottom).

Ciliates can be studied at synchronized stages representative of either the vegetative stage (WT) accumulating 23-nt siRNAs or of the sexual stage (T0) accumulating 25-nt long scnRNA uniquely involved in DNA elimination. No commercial antibody is available against ciliate AGO/PIWI proteins. Nonetheless, 5'-end labelling by PNK following purification according to the method of the invention shows a specific and strong enrichment, in the E fraction of cognate 25-nt scnRNA species in sexual stage cells. These are otherwise barely detectable, if at all, in the I and HS displaying instead strong labelling of longer RNAs.

Similar analyses were performed in two key staple crops using 5'-end labeling of sRNAs purified from lysates of rice leaves and cassava storage roots according to the method of the invention. Rice, unlike *Arabidopsis,* has a waxy leaf cuticle not favorable to RNA extraction. The rice genome is also much more replete in transposons and repeats such that the 24-nt siRNAs are disproportionately abundant. The results of 5'-end labelling after RISCs purification according to the method of the invention is in full agreement with this notion, showing a strong 24-nt sRNA and more moderate 21-nt sRNA enrichment in the E compared to the I and HS fractions. A second analysis involved lysate of cassava storage roots, which, due to their extremely high starch content, constitute an even more challenging tissue for RNA extraction. The cassava used for the analysis is a farmer-preferred genotype grown in Africa. As already observed in *Arabidopsis* and rice, 5'-end labelling following RISCs purification according to the method of the invention showed a strong enrichment in 21-nt and 24-nt sRNA species and a near-absent background in the E, but not in the I or HS fraction. Importantly, and unlike in *Arabidopsis,* no antibody is currently available against cassava AGO proteins, precluding RISC isolation via immunoprecipitation. These results demonstrate that the purification according to the method of the invention allows fast and robust isolation of RISCs from crops notoriously recalcitrant to RNA extraction and for which no AGO antibody is available.

Similar analysis were conducted in a variety of fungal and metazoan samples ranging from unicellular yeast to more complex organisms such as whole *C. elegans* or mouse whole organs. In fission yeast, heterochromatic siRNAs derived from pericentromeric repeats constitute the largest, if not unique, bulk of sRNAs. Their size is less well defined than in other organisms, but still around 23-nt. The 5'-end labelling by PNK, following RISC purification according to the method of the invention, shows a very strong enrichment of 23-nt siRNAs in the E compared to I and HS fractions displaying instead labelling of longer RNAs. This result is remarkable because *S. Pombe*'s heterochromatic siRNAs are typically undetectable by northern analysis, even using sRNA species-specific radiolabeled probes.

Worms possess a complex sRNA machinery involving more than 25 proteins in the AGO/PIWI family for which only few commercial antibodies are available and reliable. As seen with all other examples, 5'-end radiolabeling of RNA reveals a strong enrichment of sRNAs in the E but not I or HS fractions following purification according to the method of the invention. Also as seen with all other organisms, the E fraction is markedly devoid of background labelling unlike the I and HS in which mostly long RNA contaminants or breakdown products are labelled.

RISCs purification according to the method of the invention have been tested mouse adult brain. 5'-end radiolabeling reveals an enrichment of sRNAs centered on 22-nt (the cognate size of mammalian Dicer products) with, again, low background in the E, unlike in the I and HS fractions in which mostly long RNA contaminants or breakdown products are labelled. To generalize the notion that the method according to the invention enables universal isolation of RISCs including that of metazoan-specific piRNAs, similar experiments were conducted on lysates from mouse testis, a tissue where piRNAs are highly expressed. As seen with all other examples, 5'-end radiolabeling reveals an enrichment of sRNAs centered on 30-nt (the cognate size of mouse piRNAs) with, again, low background in the E, unlike the I and HS fractions in which mostly long RNA contaminants or breakdown products are labelled.

We conclude from all these analyses that the purification according to the method of the invention can be used for fast and robust isolation of RISCs across all kingdoms of life including from tissues notoriously recalcitrant to RNA extraction. The RISCs co-purify with their cognate cargoes, be they siRNAs, miRNAs, piRNAs, or scnRNAs defining the full range of all currently known silencing small RNAs.

Example 3

RISC-Associated sRNAs Purified by the Method of the Invention are Directly Amenable to Silicate-Based Extraction, Bypassing Precipitation Step As described above, the method according to the invention allows access to RISCs-associated sRNAs. Following sample lysis, the E fraction can be generated in 15 minutes, from which sRNAs are usually extracted directly although this fraction might be also stored at −80° C. (the AGO/PIWI-bound sRNA are particularly resilient to degradation).

sRNA are commonly extracted from RISCs with phenol followed by alcohol precipitation which takes a minimum of 90 minutes to a full day in total (FIG. 4A), effectively the longest step in the downstream procedure before sRNA can be used for northern, RT-qPCR, microarray analyses or deep-seq. To substantially reduce the time needed to extract sRNAs from the RISCs isolated via the method corresponding to the invention, its compatibility with commercially available silicate-based RNA purification/extraction kits was tested. The principle of these kits invariably relies upon RNA binding to silicate matrices in the presence of alcohol and salts (based on hydrophobicity) followed by elution in small volumes of RNase-free water or buffer.

Figure 4:
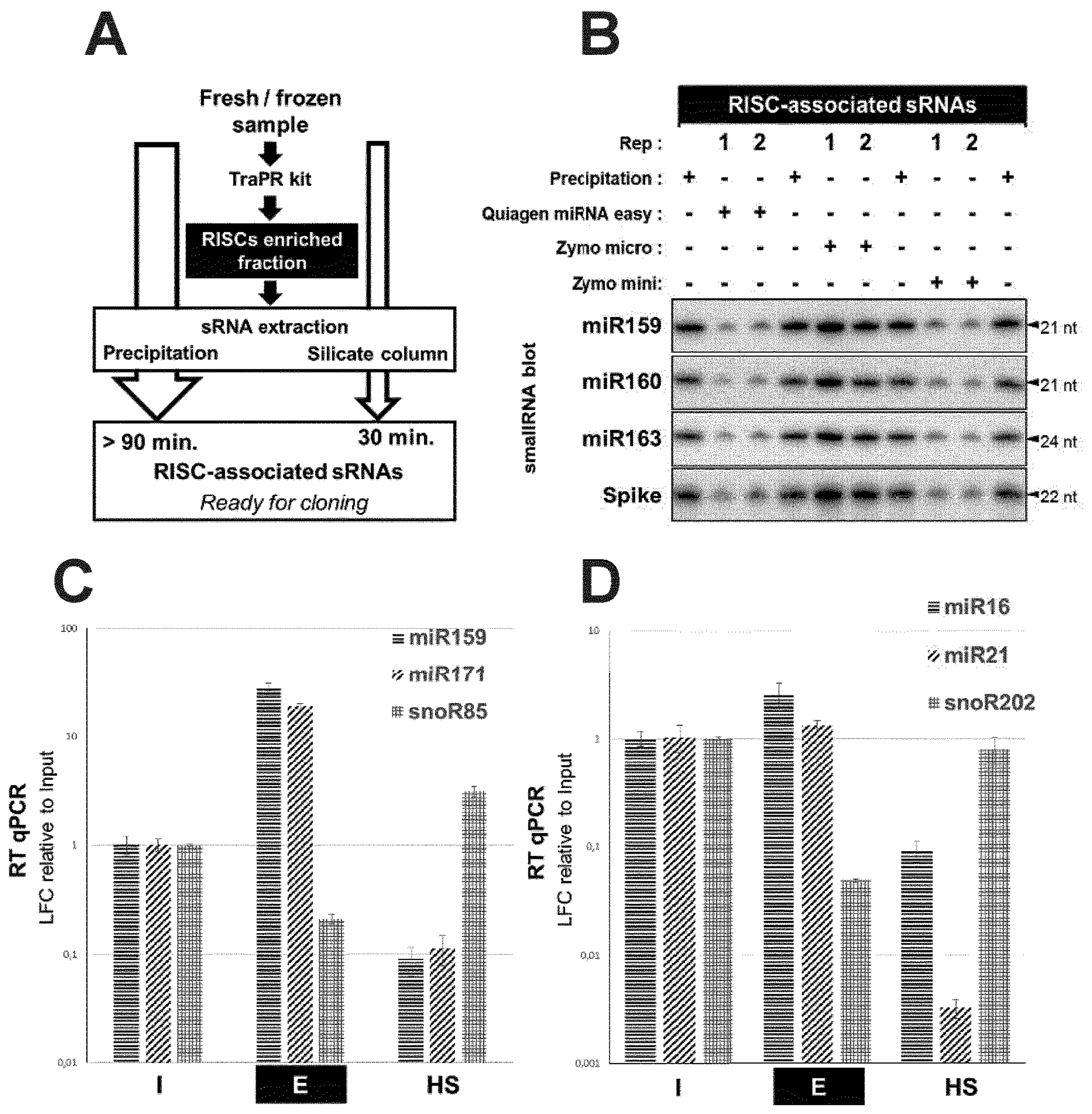
FIG. 4A shows a schematic view of the workflow to isolate RISC-associated sRNAs according to one embodiment of the invention's method whereby sRNAs are recovered using commercial silicate-based columns (right) instead of the standard precipitation (left). The approximate duration of each sRNAs recovery process is indicated.
FIG. 4B shows a comparative Low Molecular Weight RNA analysis, on a 17% denaturing polyacrylamide gel, of *Arabidopsis* inflorescence RISCs-associated sRNAs extracted according to one embodiment of the invention's method whereby sRNAs are recovered using commercial silicate-based columns instead of the standard precipitation. Specific known *Arabidopsis* sRNA species were detected as explained in FIG. 2G. Two replicates are shown for each commercial kit tested. Spike is a synthetic 22-nt RNA sequence added in each fraction post-purification as a control for the RNA extraction step.
FIG. 4C shows a quantitative RT-PCR analysis of miR159 and miR171 abundance in *Arabidopsis* inflorescence samples (n=3) from which RISCs were extracted according to the method of the invention. The expression is shown as relative to the detection levels in crude lysates (I fraction). snoRNA 85 was used as a control for a non-RISC loaded RNA (I: clarified lysate, E: RISCs fraction, HS: High salt wash of the resin after AGOs elution).
FIG. 4D shows a quantitative RT-PCR analysis of miR16 and miR21 from mouse liver samples (n=3). snoRNA 202 was used as a control for a non-RISC loaded RNA (I: clarified lysate, E: RISCs fraction, HS: High salt wash of the resin after AGOs elution).

FIG. 4A provides an overview of the workflow designed to plug-in the silicate-separation into the RISC-associated sRNAs purification procedure according to the invention. Three manufactured silicate-based purification systems were tested against the standard alcohol-based precipitation procedure: Qiagen™ RNAeasy, Zymo™ micro and Zymo™ mini Ic columns. RISCs-associated sRNAs isolated from *Arabidopsis* inflorescences according to method of the invention were used in that case, and the final sRNA yields were evaluated by northern analysis of known miRNAs (miR163, miR160, miR159). As shown in FIG. 4B, the best yield—on par with that of precipitation—was obtained when the RISC-associated sRNAs purified according to the invention were used in conjunction with the Zymo™ micro Ic column. The other columns tested showed significantly lower sRNA outputs, probably reflecting the loss-of-material during the immobilization/elution steps.

The coupling of Zymo™ micro columns decreases (30 minutes) the time required to access RISC-associated sRNAs according to the method of the invention (FIG. 4A). Moreover, due to its design, the Zymo™ micro Ic column allows the recovery of sRNA in a small volume of water highly suitable to direct molecular analysis such as reverse transcription prior to quantitative PCR or sRNA library preparation for Deep-seq. Using this experimental set up, RISC-associated sRNAs isolated according to the method of the invention allows a large number of samples to be processed within record time following their lysis.

RISC-Associated sRNAs Purified by the Method of the Invention are Highly Suitable for miRNA Detection Via RT-qPCR in Various Biological Systems Deep-seq remains a gold standard to identify and quantify, at the whole-genome scale and without a priori, the sRNA populations within a given biological sample. Despite its increasing affordability, (economically and technically) the systematic use of Deep-seq to investigate biological processes or for mere diagnosis is still prohibitive for most research laboratories, notwithstanding the expertise required for large sRNA data curation/analysis. In most cases, Deep-seq is used as a downstream procedure for identifying robust sRNA candidates linked to a particular process, cellular state or pathology. Once such candidates are validated, the preferred downstream method relies upon targeted RT-qPCR-based quantification of these sRNA candidates as opposed to genome-wide sRNA sequencing. RT-qPCR allows accurate quantification of multiple sRNA sequences on a large number of samples, at a modest cost.

The main limiting aspect of RT-qPCR-based sRNA quantification is the reverse-transcription (RT) step, where specific sRNA sequences are reverse-transcribed into cDNA to enable the downstream PCR amplification. The complexity of the RNA preparation including the potential low abundance of the sRNA sequence of interest might indeed compromise the RT efficiency, thereby negatively impacting the quality and robustness of quantification. Given that the purification according to the method of the invention dramatically enriches RISC-associated sRNAs in the E fraction, its suitability for miRNA quantification was tested using an in-house loop-based RT-qPCR procedure on sRNAs purified from *Arabidopsis* inflorescences. With the RISC-associated sRNAs purification according to the method of the invention, the miRNAs tested (miR159, miR171) were enriched in the E compared to HS fraction. The HS fraction was, by contrast, enriched in the *Arabidopsis* small nucleolar RNA snoRNA85, which is not loaded into any AGO (FIG. 4C). In a second example involving a sRNA-rich mammalian tissue such as the mouse liver, a similar pattern was observed with the enrichment of two mammalian miRNAs in the E fraction and of snoRNA202 in the HS fraction, respectively (FIG. 4D). Altogether, these results demonstrate that RISC-associated sRNAs purified according to the method of the invention are highly suitable for miRNA detection via RT-qPCR in different biological systems.

Example 4

Figure 5:
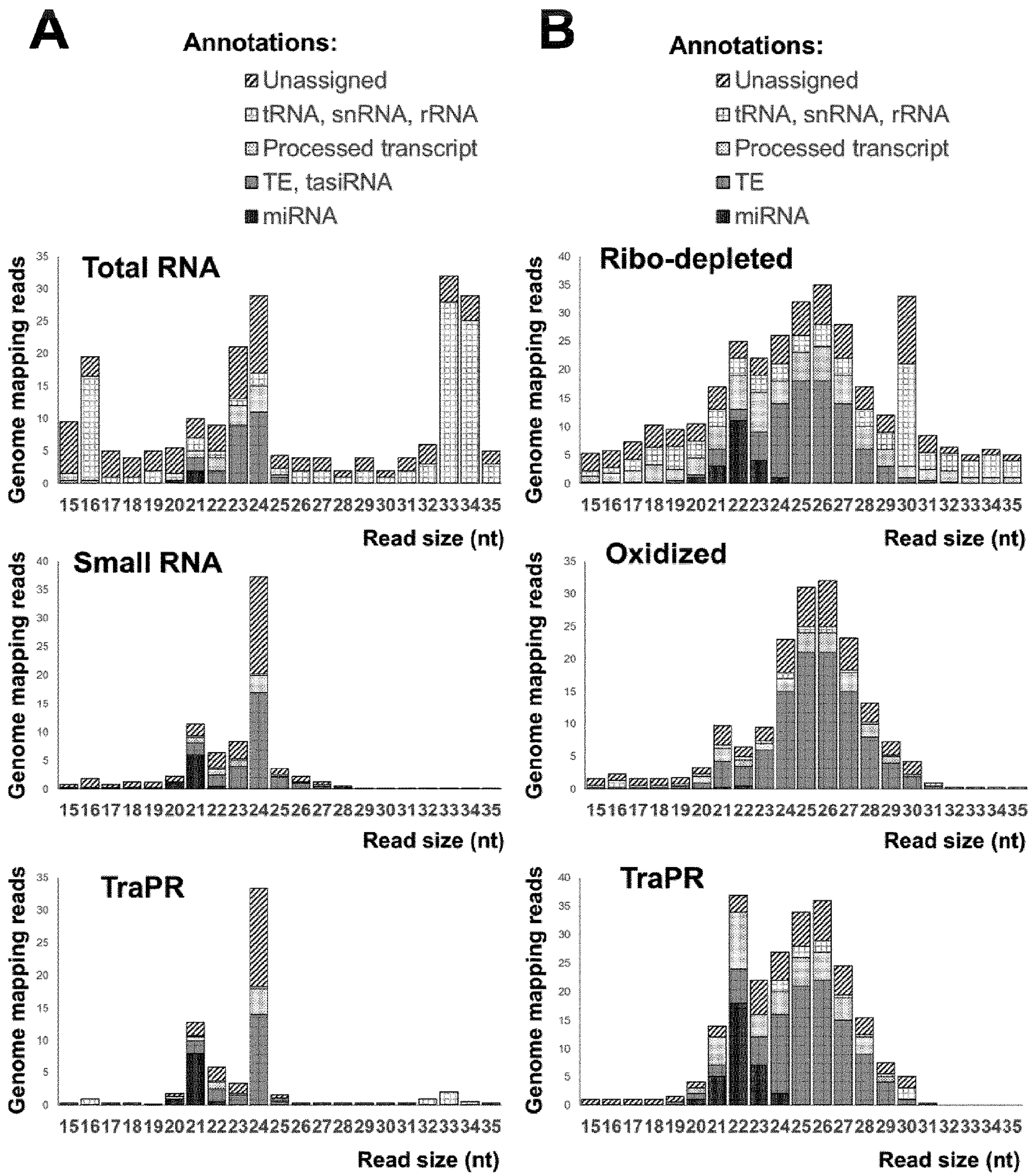
FIG. 5A shows the length distribution and genomic origin of *Arabidopsis* inflorescence RNA following TRUseq based sequencing of total RNA (top), polyacrylamide gel-selected sRNA (middle) or purified RISCs-associated sRNAs extracted according to the method of the invention (bottom) (n=3 for each condition).
FIG. 5B shows the length distribution and genomic origin of *Drosophila* ovary RNA following a custom made sequencing protocol of polyacrylamide gel-selected, ribodepleted sRNAs (top), or additionally subjected to oxidization (middle), or purified RISCs-associated sRNAs extracted according to the method of the invention (bottom) (n=2 for each condition).

RISC-Associated sRNAs Purified by the Method of the Invention are Directly Amenable to Deep-Seq in a Range of Organisms As shown using radiolabeling of RNAs in FIG. 2, RISC-associated sRNAs purification according to the method of the invention applied, for instance, to *Arabidopsis* samples, yields strongly enriched sRNAs simultaneously depleted of other nucleic acid contaminants. In the state of the art, sRNA size selection on polyacrylamide gel is an absolute prerequisite for sRNA library preparation destined for deep-seq. This step, required for optimal outputs, is seldom used for fear of sample loss in other models such as conventional mammalian tissues. Indeed, gel-based size excision is a long, tedious procedure of high technicity requiring, moreover, the use of radiolabeled RNA size rulers, and generally providing a low output of sRNA material for downstream analyses (e.g. RT-qPCR or Deep-seq). Due to the systematic, substantial enrichment in RISC-associated sRNAs in the E fraction yielded by the method according to the invention, a test was made to check if the method can bypass gel selection altogether in the production of Deep-seq-ready sRNA libraries in two notoriously difficult cases (FIG. 5). *Arabidopsis* and *Drosophila* are indeed two organisms in which abundant contaminating low molecular weight RNAs imposes the use of gel-based size excision for library preparation.

Analyses in *Arabidopsis* were conducted in three technical triplicates from the same batch of inflorescences. We compared the results of deep-seq from sRNA isolated via of three independent gel size selection events, three independent TRIzol-based extraction of total RNA, or three independent batches of RISC-associated sRNAs purified according to the method of the invention without size selection on gel (FIG. 5A). The libraries were generated with the TRUseq (Illumina) library preparation kit. Upon curation and trimming, the sRNA read size distribution obtained after gel size selection displays the expected profile for plant sRNAs, with two peaks at 21-nt (miRNAs) and 24-nt (heterochromatic siRNAs) (FIG. 5A, middle). As expected, direct cloning from total RNAs (FIG. 5A, top) in complex biological models such as *Arabidopsis* is incompatible with quality library preparation. The two sRNA peaks are either barely visible (21-nt) or poorly defined (24-nt). Moreover, they are surrounded by major contaminants within the same size range accounting for >60% of the reads in each of the three libraries. By contrast, the size profile obtained with the three samples independently purified with the method of the invention without gel size-selection clearly shows the 21-nt and 24-nt peaks expected for *Arabidopsis* with barely any contaminant (FIG. 5A, bottom). The sequencing results obtained with RISC-associated sRNAs purified according to the method of the invention are not only on par with those obtained after size selection on gel, but they also show less variations between replicates, most likely reflecting the bare minimal sample handling requirements and overall robustness of the method.

Comparative deep-seq analyses were also conducted on *Drosophila* ovaries in which extraction and cloning of sRNAs provides a high-level benchmark in terms of difficulty and tediousness. In this complex tissue, three sRNAs classes are found: 22-nt miRNAs and 21-nt siRNAs are respectively loaded into AGO1 and AGO2. By contrast, the metazoan-specific piRNAs, 23-to-29-nt in length, are loaded into PIWI proteins. piRNA sequencing has been very much optimized in the fly, due to the highly abundant 2S rRNA (30-nt) in the same size range. The current, laborious, procedure entails first to gel-select, in a very precise manner, sRNAs with a length comprised between 18 and 29 nucleotides. In a second step, the purified sRNAs are ribo-depleted using commercial kits, then oxidized in order to remove RNA not harboring a 3' methyl group. Metazoan siRNAs and piRNAs harbor this modification and are thus protected from oxidization unlike miRNAs or the 2S rRNA. A major caveat is that, after oxidization, the sample is depleted not only from the main contaminant (2S), but also from the information encoded by miRNAs, which is highly valuable nonetheless.

Figure 6:
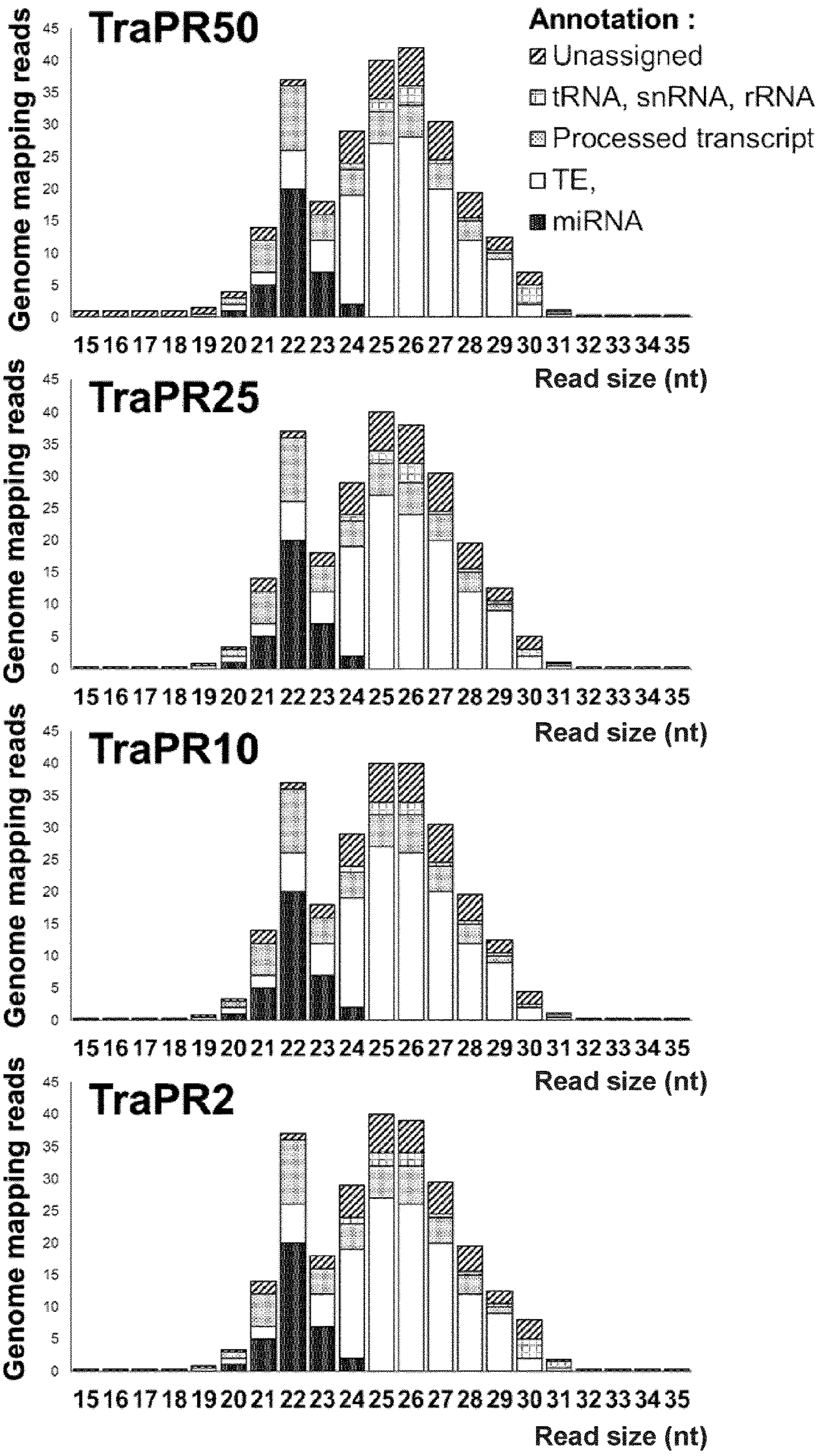
FIG. 6 as in FIG. 5B according to the method of the invention applied to 50 (TraPR50), 25 (TraPR25), 10 (TraPR10) or 2 ovaries pairs (TraPR2) (n=2 for each condition).

In a second set of experiments, a deep-seq analysis was conducted on RNA from *Drosophila* ovaries. Libraries were generated in biological duplicates using an optimized in-house cloning procedure developed in the Brennecke laboratory (IMBA, Vienna), in which gel selected sRNAs are ribodepleted, then oxidized. This golden standard was compared to direct cloning of RISC-associated sRNAs purified according to the method of the invention without any ribodepletion and oxydization (FIG. 5B). In order to test the performance of the method according to the invention on a wide range of input, libraries were prepared from 2, 5, 10, 25 and 50 ovary pairs (FIGS. 5B and 6). The compared size profiles of mapped reads obtained from the different strategies are presented in FIG. 5B, showing the presence of both miRNA and 2S rRNA in libraries of gel-selected and ribodepleted but non-oxidized RNA (FIG. 5B, top) and their strong reduction upon oxidization (FIG. 5B, middle). In all libraries obtained after direct cloning of RISC-associated sRNAs according to the method of the invention, miRNAs are present, however, but a strong depletion of the contaminating 2S rRNA is observed (FIG. 5B, bottom). Remarkably, a near-identical profile is observed for the purified RISC-associated sRNAs independently of the amount of starting material, demonstrating the robustness and consistency of the method over a broad range of input quantities (FIGS. 5B bottom and 6).

Figure 7A:
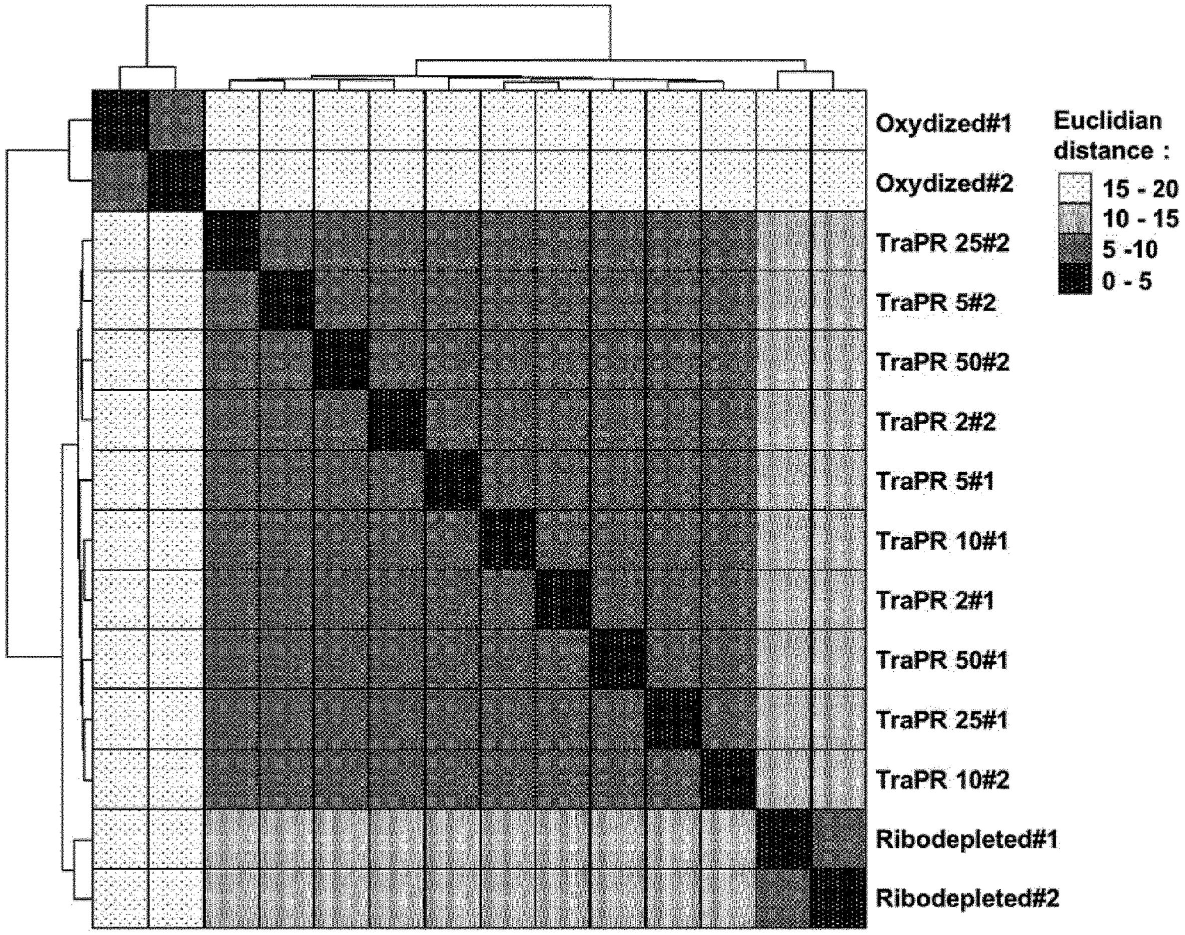
FIG. 7A shows a clustering analysis of individual custom made sequencing libraries prepared in FIG. 5B and FIG. 6, based on the identity and abundance of all known *Drosophila* miRNAs.

A clustering analysis was conducted on the miRNA content of the three library types. The heatmap in FIG. 7A shows that the gel selected, ribodepleted and oxidized libraries cluster together as outlayers, as expected, due to the loss of miRNAs induced by the treatment. By contrast, the gel selected and ribodepleted sRNA libraries cluster close to the RISC-associated sRNAs libraries. Finally, the individual libraries generated from different amount of starting material using the method of the invention cluster together, independently of the amount of starting material used. This result confirm that the method of the invention allows the generation of robust and comparable RISC-associated sRNA libraries on a broad range of input.

One recurring and legitimate question raised by the use of the method of the invention concerns the qualitative and quantitative correlation of sRNA content yielded by the various procedures. In other words, by selecting exclusively functional i.e. RISC-associated sRNAs, does the method according to the invention induce an underrepresentation or a loss of certain sRNA species isolated via other methods? To address potential biases, a correlation analysis was conducted on the sRNA content of all *Drosophila* libraries (FIG. 7B).

Figure 7B:
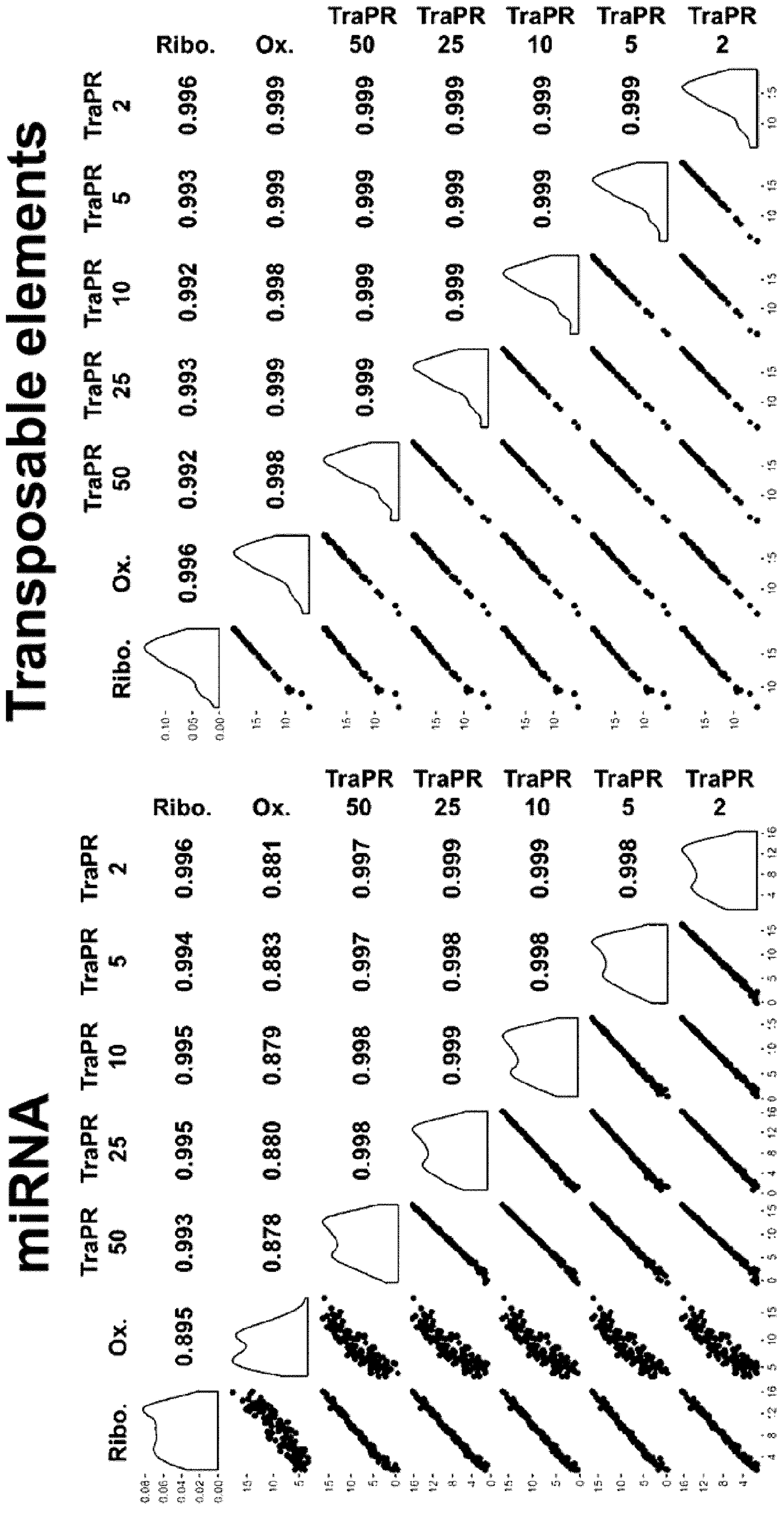
FIG. 7B shows a correlation analysis of miRNAs (left) and sRNAs mapping to transposable elements (right) based on their identity and abundance in the libraries prepared in FIG. 5B and FIG. 6 (n=2).

Taking ribodepleted sRNA libraries as reference, a good correlation (>0.99) is observed when comparing the miRNA- and TE-mapping reads (piRNAs and siRNAs) between the ribodepleted and RISC-associated sRNAs libraries (FIG. 7B. As expected from the previous analysis, the miRNA population is lost in the Oxidized sRNA libraries, in contrast to siRNA and piRNA populations which show a high correlation between the three procedures. Altogether, these results show that the RISC-associated sRNA purification according to the method of the invention does not induce biases in the representation of sRNAs in sequencing libraries. The remarkably high correlation between the different RISC-associated sRNA libraries for miRNAs and TE-mapping sRNAs confirms the robustness and consistency of the method of the invention, independently of the amount of starting material used.

Example 5

Figure 8:
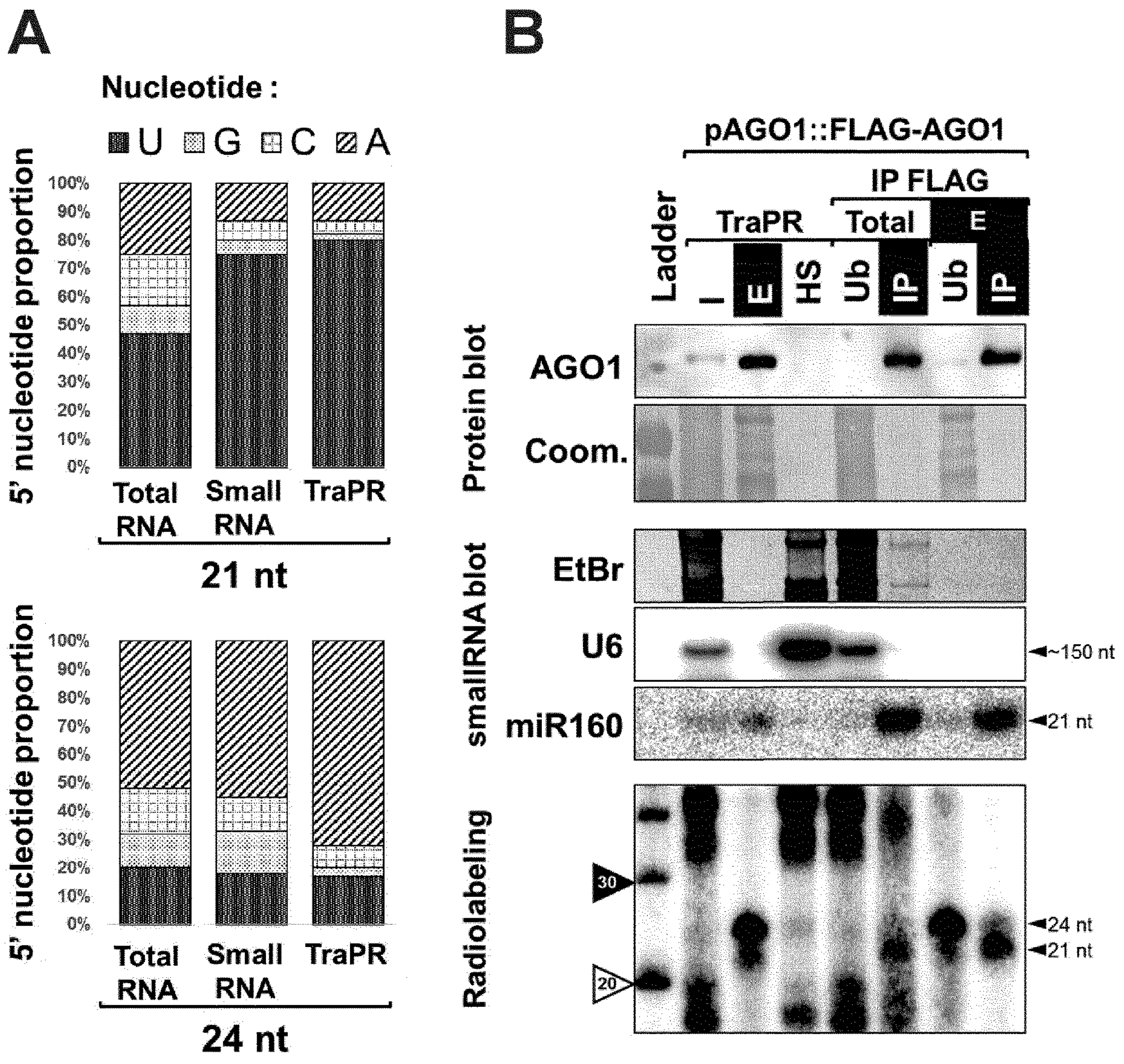
FIG. 8A shows the 5' nucleotide composition of total RNA, gel extracted sRNAs or RISCs-associated sRNAs extracted according to the method of the invention as in FIG. 5A. Nucleotide identity is displayed for 21-nt long (top) and 24-nt long (bottom) sRNAs (n=3 for each condition).
FIG. 8B shows a protein blot analysis of *Arabidopsis* Flag-AGO1 expressed under the AGO1 endogenous promoter extracted from inflorescences according to the method of the invention and detected with an anti-AGO1 antibody (top panel, TraPR) (I: clarified lysate, E: RISCs fraction, HS: High salt wash of the resin after AGOs elution). Alternatively, (top panel, IP Flag) Flag-AGO1 was immuno-precipitated from the clarified lysate (total) or the RISCs-containing fraction according to the method of the invention (Ub: unbound, IP: immuno-precipitation). The middle panel depicts a Low Molecular Weight RNA analysis, on a 17% denaturing polyacrylamide gel, of *Arabidopsis* miR160 detected as in FIG. 2G. The bottom panel shows an RNA blot analysis, on a 17% denaturing polyacrylamide gel, of *Arabidopsis* inflorescence RISCs-associated sRNAs as in FIG. 2F. Ambion® DECADE™ was used as a sRNA size ruler (nucleotides).

The Method of the Invention Isolates Native RISCs and Improves the Quality of Immunoprecipitation In *Arabidopsis*, AGO1- and AGO2-clade AGOs preferentially associate with 21-nt long sRNA species starting with a 5' Uracil (U) whereas the AGO4 clade associates preferentially with 24-nt species starting with a 5' Adenine (A). To confirm that the native RISC purification enabled by the method of the invention is applicable to the complete suite of *Arabidopsis* AGO proteins, a 5' nucleotide analysis was conducted using the sRNA sequencing libraries presented in FIG. 5. The comparison of the proportion of nucleotides found in 5' extremities of 21-nt (FIG. 8A, top) and of 24-nt (FIG. 8A, bottom) species was conducted based on libraries generated from gel-size selected sRNAs, total RNA, or RISC-associated sRNAs purified according to the method of the invention. The analysis reveals a strong 5' U bias for 21-nt species and 5' A bias for 24-nt species, in both gel selected and RISC-associated sRNAs libraries, confirming that the latter procedure isolates genuine, functional AGO-sRNA complexes. In fact, the enrichment in cognate 5'A/U terminal sRNAs seems even more stringent in the library generated from RISC-associated sRNAs purified according to the method of the invention, compared to sRNA size-selected on gel (FIG. 8A).

The method according to the invention isolates functionally active pools, i.e. AGO-loaded, sRNAs and, as such, infers the purification of native RISCs. To confirm the native state of isolated RISCs, *Arabidopsis* AGO1 immunoprecipitation (IP) experiments were conducted in parallel from total lysates or RISCs-enriched E fractions isolated according to the method of the invention. The experiment was conducted in inflorescences from a transgenic *Arabidopsis* line expressing Flag-tagged AGO1 under its endogenous promoter, which is detected with a commercial anti-Flag antibody. The protein blot presented in FIG. 8B (top) shows that AGO1 is efficiently immunoprecipitated in both total lysate and the RISCs-enriched E fraction according to the method of the invention. In both conditions, the absence of an AGO1 signal in the unbound fraction (Ub) shows that the Flag IP is highly efficient. In *Arabidopsis,* AGO1 preferentially loads approx. 21-nt miRNA and indeed, with both procedures, miR160 is enriched in the immunoprecipitated fraction, confirming its interaction with AGO1 as part of a native RISC (FIG. 8B, middle). 5'-end radiolabeling of the RNA in each fraction shows an enrichment of discrete, 21-nt-long sRNA species in the IP from total lysates, albeit accompanied by non-specific background labeling due to contaminating RNA (FIG. 8B, bottom). By contrast, labeling of sRNA immunoprecipitated from the RISCs-enriched E fraction isolated according to the method of the invention shows little background and a strong, specific enrichment of 21-nt RNA species in the IP fraction as opposed to 24-nt species remaining in the unbound fraction and preferentially loaded into AGO4-clade proteins. The low levels of RNA contaminants found in the AGO1 IP conducted from the RISCs-enriched E fraction is likely explained by the subtraction of non-RISC-associated RNA inherent to the method of the invention, prior to the IP. Altogether, these results confirm that RISCs are purified in their native state using the method of the invention, which is therefore compatible with downstream immunoprecipitation of AGO proteins. The non-RISC-associated RNA depletion in the E fraction can thus be considered a valuable clean-up step such that the method according to the invention may also be used to generally improve the quality of AGO IP experiments in plants and, presumably, other organisms.

Example 6

RISC-Associated sRNAs Purified by the Method of the Invention are Highly Resilient to Degradation RNAs are unstable molecules sensitive to degradation at any step of their preparation and handling, from sample collection to long-term storage. Although their loading into AGO proteins makes the regulatory sRNAs more stable than other RNA species, the degradation products of long RNA will strongly contaminate sRNA libraries prepared from samples of suboptimal quality via total RNA or sRNA gel-size selection. Since the method of the invention isolates RISCs in which sRNAs are bound to their cognate AGO effectors, its use was anticipated to strongly select against longer RNA degradation products found in suboptimal quality samples, thereby potentially enabling high quality sRNA deep-seq libraries to be prepared even from highly degraded RNA preparations. To test this idea, the non-clarified lysate from a mouse liver was treated with RNase T1 and incubated at room temperature for 30 minutes before being subjected to sRNA purification according to the method of the invention. Deep-seq libraries were prepared in biological triplicates, from input (total RNA) and RISC-associated sRNAs, using intact or RNAse-treated samples.

Figure 9:
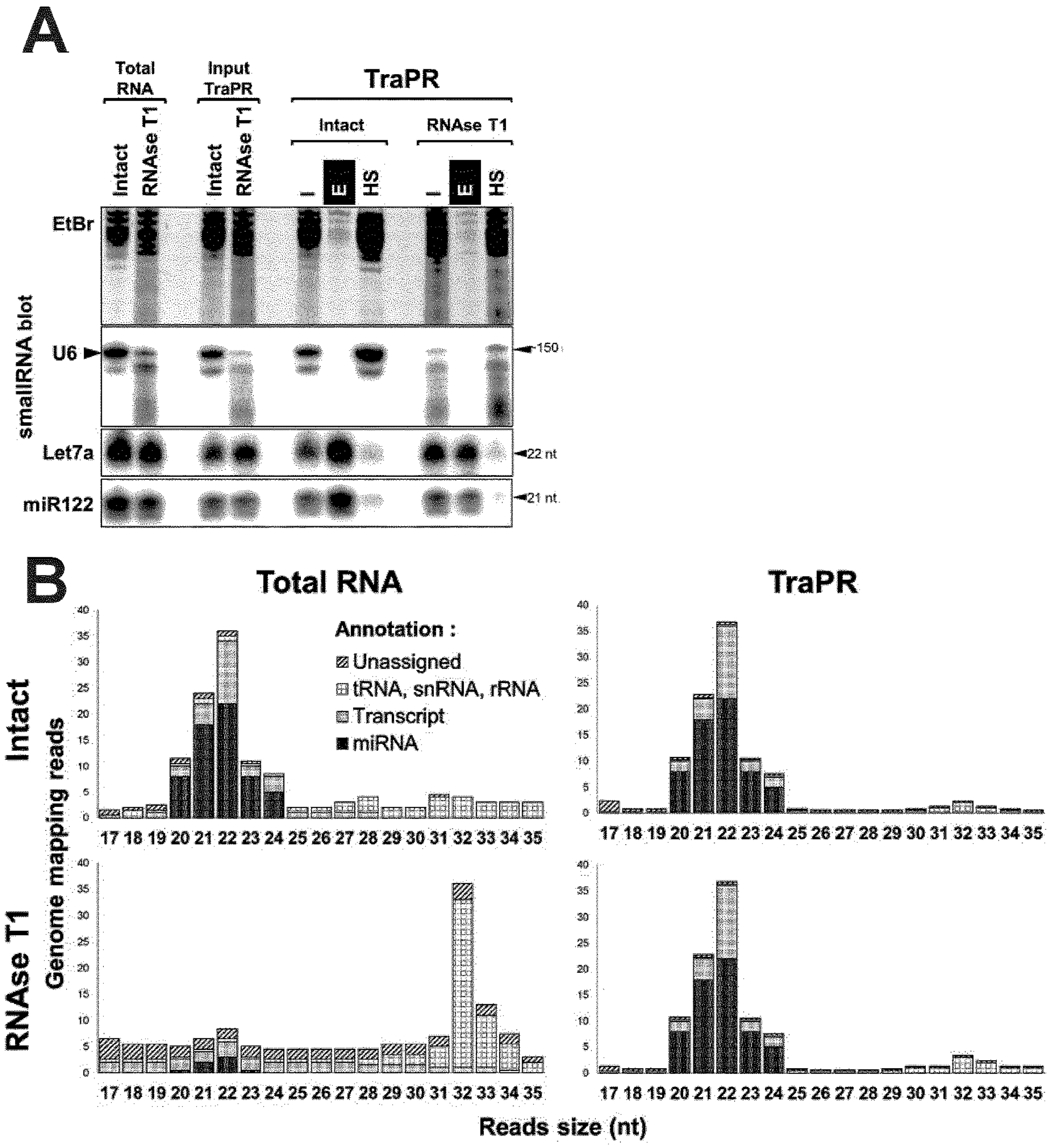
FIG. 9A shows a Low Molecular Weight RNA analysis, on a 17% denaturing polyacrylamide gel, total RNA (Total RNA) and RISCs associated sRNA purified according to the method of the invention (TraPR) from mouse liver intact or treated with 100U RNAse T1 during 30 minutes at room temperature (I: clarified lysate, E: RISCs fraction, HS: High salt wash of the resin after AGOs elution).
FIG. 9B shows the length distribution and genomic origin of mouse liver RNA following TRUseq based sequencing of total RNA of mouse sRNA libraries generated with total RNA (left) or RISCs-associated sRNAs purified according to the method of the invention (TraPR, right), from intact (top) and RNAse T1-treated (bottom) mouse liver (n=3 for each condition).
FIG. 9C shows a correlation analysis of miRNAs based on their identity and abundance in the libraries prepared in FIG. 9B (n=3).

Prior to deep-seq, low molecular weight RNA blot analysis was conducted (FIG. 9A). It shows that AGO-bound sRNAs isolated according to the method of the invention such as Let7a or the hepatocyte-specific miR-122 are readily detected in either the intact or RNAse T1-treated samples despite strong degradation of other RNAs. This degradation is evidenced by ethidium bromide staining of the acrylamide gel before transfer of nylon membrane and is also visible after hybridization of the generic U6 RNA, which displays as a "ladder" in all RNase T1-treated samples. Note that these abundant degradation products spawned from U6- and ethidium bromide-stained longer RNA species are within the size range of silencing sRNAs and, as such, likely contaminate the sRNA libraries prepared via total RNA extraction or even size selection on gel.

This notion was indeed confirmed upon inspection of the sequencing results from the sRNA libraries prepared with the standard Truseq (Illumina) procedure. The annotation profile in FIG. 9B reveals the strong negative impact of RNA degradation (RNase T1 treatment) on the quality of sRNA libraries prepared directly from total RNA: such libraries are consistently highly contaminated by up to 80% of tRNA-derived fragments, reducing the amount of sequenced miRNAs by almost one-order-of magnitude compared to the libraries prepared from intact liver samples. By contrast, RISC-associated sRNA libraries prepared according to the invention are only modestly affected by degradation and show a comparable quality to those prepared without RNase-T1 treatment. In both RISC-associated sRNA libraries, the genome-mapping reads are predominantly miRNAs centered on 22-nt, independently of the degraded status of the sample, This peak is, by contrast, almost undetectable in degraded samples following total sRNA extraction due to a large tRNA contamination peaking at 32-nt that likely impinges on the cloning of silencing sRNAs.

Figure 9C:
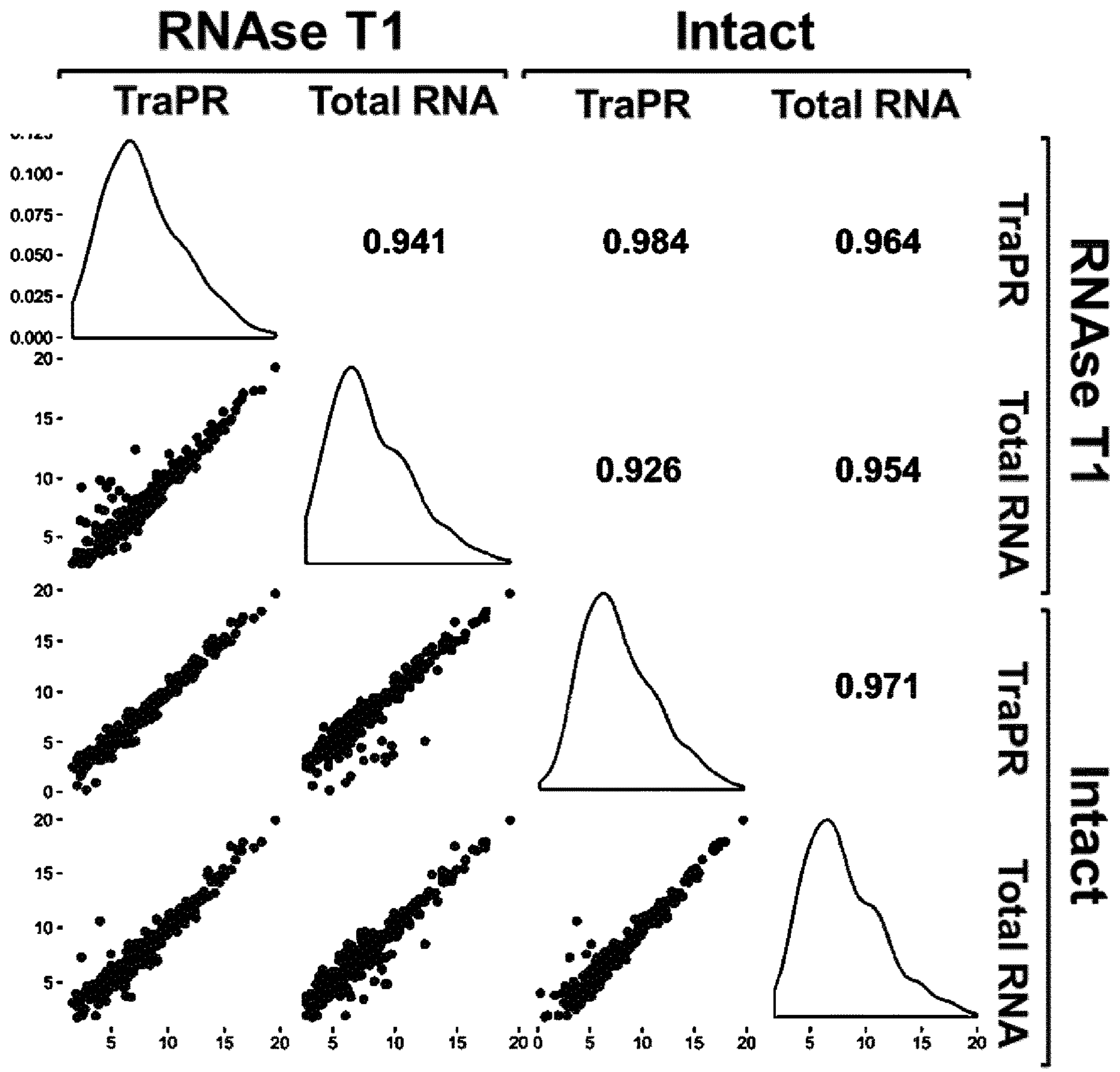

To test potential biases of the method according to the invention when it is applied to degraded samples, a correlation analysis was conducted with the sRNAs sequenced from the various libraries. The results presented in FIG. 9C demonstrate that the miRNA pool isolated via the method according to the invention applied to RNase T1-treated samples remains unbiased (correlation=0.984) compared to the pool isolated from intact samples or isolated after total RNA preparation without RNAse T1 treatment (correlation=0.954). Therefore, by purifying AGO-loaded sRNAs prior to library preparation, the method of the invention allows highly accurate sample comparison independently of their respective degradation state.

This result is highly relevant for work conducted with unstable samples, samples collected at various time intervals and/or stored under various conditions including some not preventing RNA degradation. The method of the invention is therefore uniquely suited to the study of large cohorts of patient-derived biopsies or biological fluids, which are prone to degradation and collected sometimes over many years (e.g. >10 years). This would normally strongly limit robust comparisons of sRNA cohorts contained in the samples via deep-seq, but the method according to the invention enables normalization of sRNA libraries through their RISCs contents.

Example 7

The Method According to the Invention Enables Highly Reproducible and Robust sRNA Isolation From Mammalian Plasma The complexity, RNA-degradation proneness and very low sRNA content of mammalian plasma has so far drastically impeded the robust exploration of sRNA biomarkers in this, and other body fluids, in clinical research. The same impediment applies to the use of RT-qPCR to reliably detect already identified circulating biomarkers for diagnosis/prognosis. We thus tested the performance of the method according to the invention with mouse plasma to assess if the procedure could remedy these major, often unsurmountable, burdens. Plasma samples were collected from four individual mice. Each sample was subjected to total RNA extraction from 150 μL of plasma, or RISCs-associated sRNA purification according to the method of the invention, from the same volume. For all conditions, the RNA was cloned following the smallRNA library preparation kit produced by Lexogen.

Figure 10:
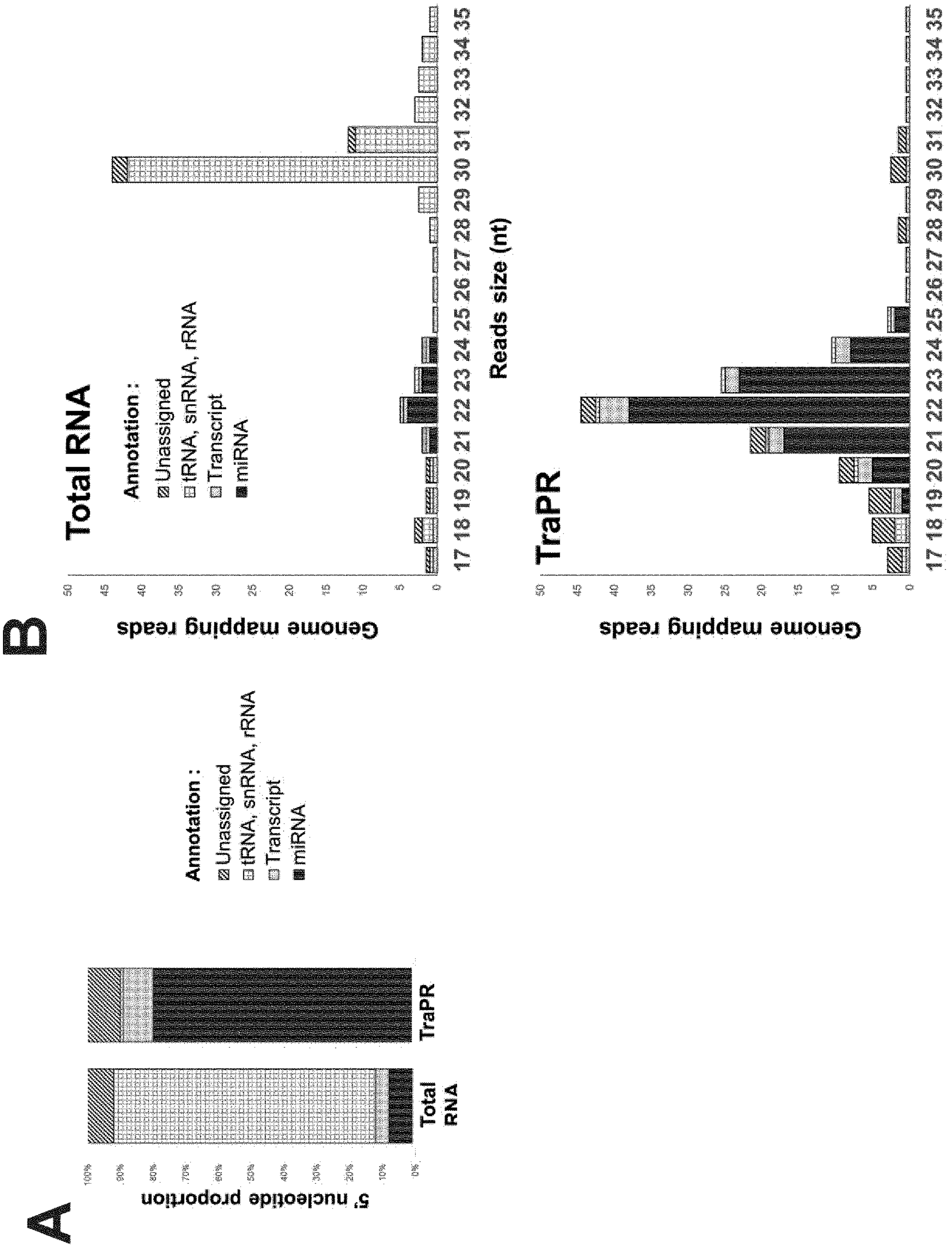
FIG. 10A shows the proportion and genomic origin of mouse sRNAs in libraries generated with the Lexogen sRNA library kit using total RNA or RISCs-associated sRNAs purified according to the method of the invention (TraPR) from mouse plasma (n=4).
FIG. 10B is the same as FIG. 10A but incorporates the sRNAs length distribution.
FIG. 10C shows the correlation of miRNA abundance in individual libraries generated as explained in FIG. 10A from total RNA (top) and RISCs associated sRNA purified according to the method of the invention (TraPR, bottom).
FIG. 10D shows the dispersion of miRNAs in libraries prepared from total RNA or RISCs-associated sRNA as explained in FIG. 10A. The dispersion is depicted in quartile according to miRNA abundance (Wilcoxon rank sum test, * $<4.5.10^{-5}$,  $<5.10^{-4}$).
Figure 10C:
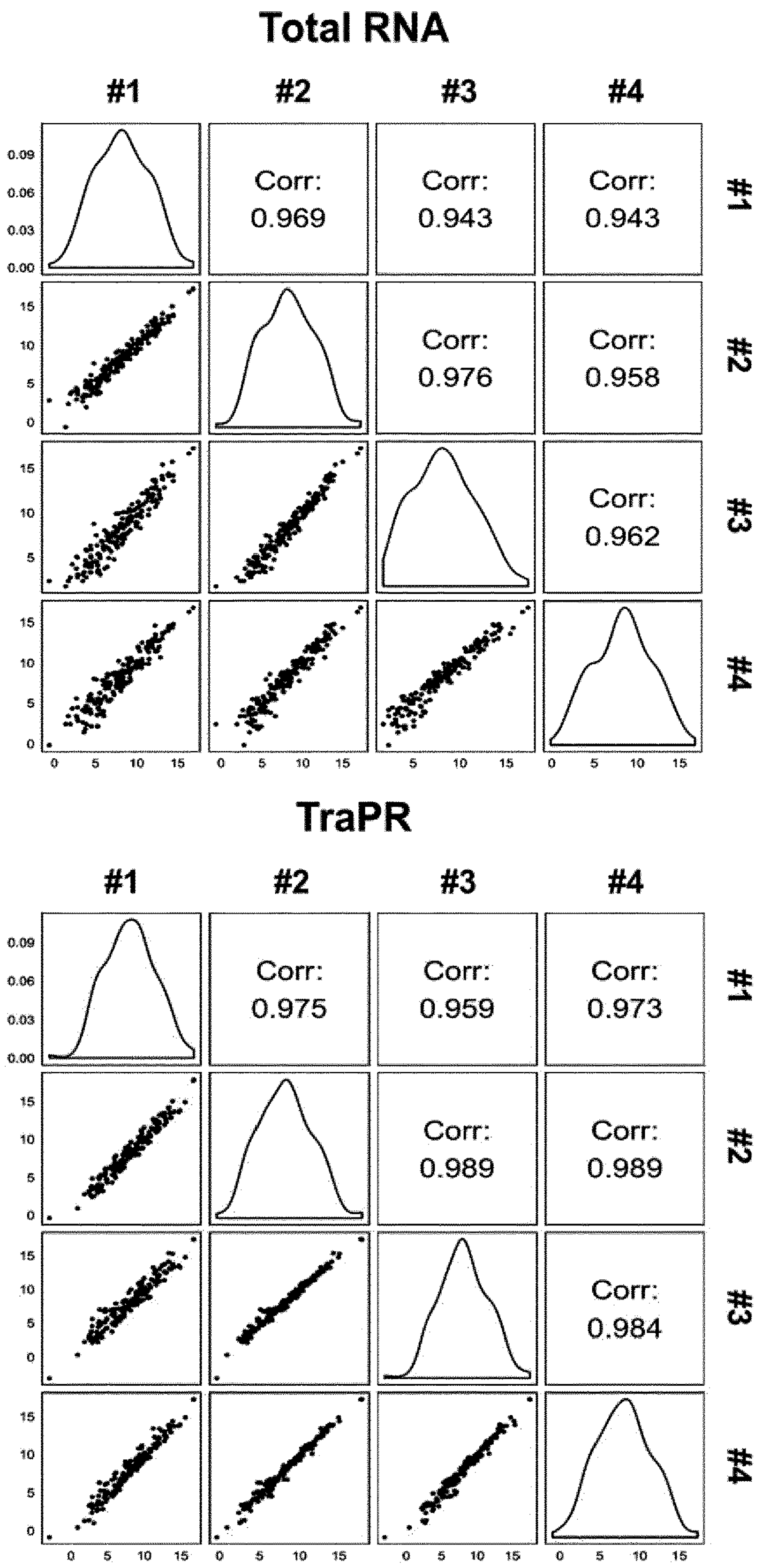
Figure 10D:
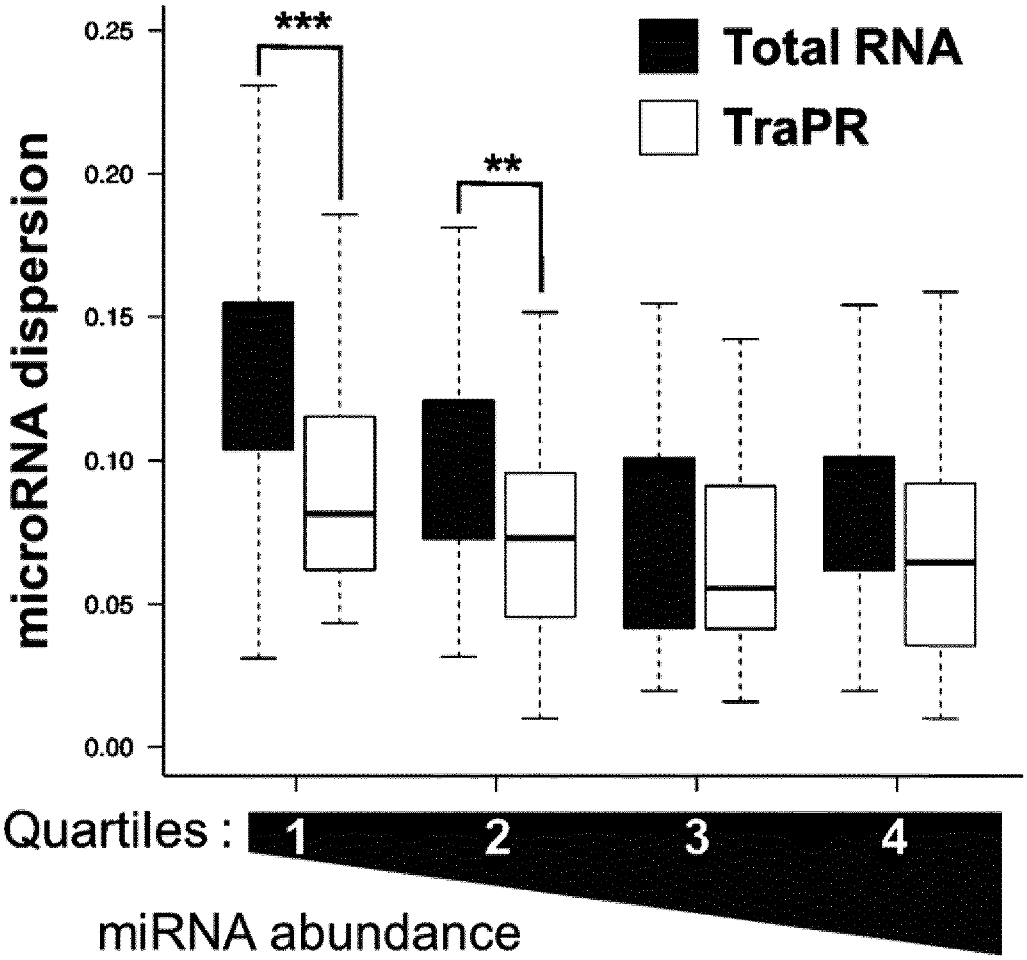

FIG. 10A shows the sequencing reads proportions, by annotation, obtained for the various plasmatic sRNA libraries. As expected, the total RNA libraries contain up to 80% of tRNA contaminants. By contrast, libraries prepared from RISC-associated sRNAs purified according to the method of the invention are highly enriched in miRNAs, representing >90% of their contents with barely any trace of contamination or degradation products. These results are confirmed by the length distribution of reads mapping to the mouse genome (FIG. 10B). Indeed, libraries from total RNA display only a minor peak centered on 22-nt (miRNAs) and, instead, a major tRNA peak centered on 30-nt, reflecting heavy contamination. By contrast, libraries of RISC-associated sRNA purified according to the method of the invention display a unique, sharp miRNA signal centered on 22-nt and accounting for all sequencing reads. Correlations analysis were conducted for miRNA populations presents in individual total RNA libraries (FIG. 10C, top) and for libraries generated from RISC-associated sRNA purification according to the method of the invention (FIG. 10C, bottom). This analysis reveals a significantly higher intra-individual correlation for miRNA populations from libraries generated after RISC-associated sRNA purification compared to total RNA libraries. Moreover, the analysis of miRNA dispersion displayed per quartile of miRNA abundance, as shown in FIG. 10D, reveals significantly less variations for low abundant miRNAs in RISC-associated sRNA libraries compared to total RNA libraries. This result shows that the method according to the invention yields significantly more comparable results for low abundant sRNA sequences in deep-seq libraries.

Figure 11:
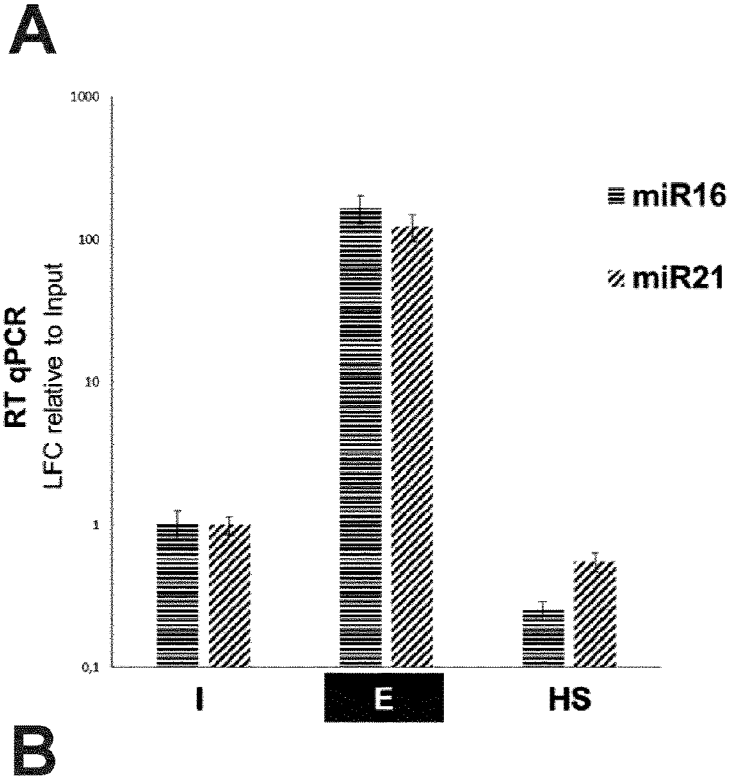
FIG. 11A shows a quantitative RT-PCR analysis of miR16 and miR21 from mouse plasma samples (n=3). (I: clarified lysate, E: RISCs fraction, HS: High salt wash of the resin after AGOs elution).
FIG. 11B shows the correlation of miRNA abundance in individual libraries generated with the Lexogen sRNA library kit (n=4) or TRUseq (n=3) using total RNA or RISCs-associated sRNAs purified according to the method of the invention (TraPR) from mouse plasma.
Figure 11:
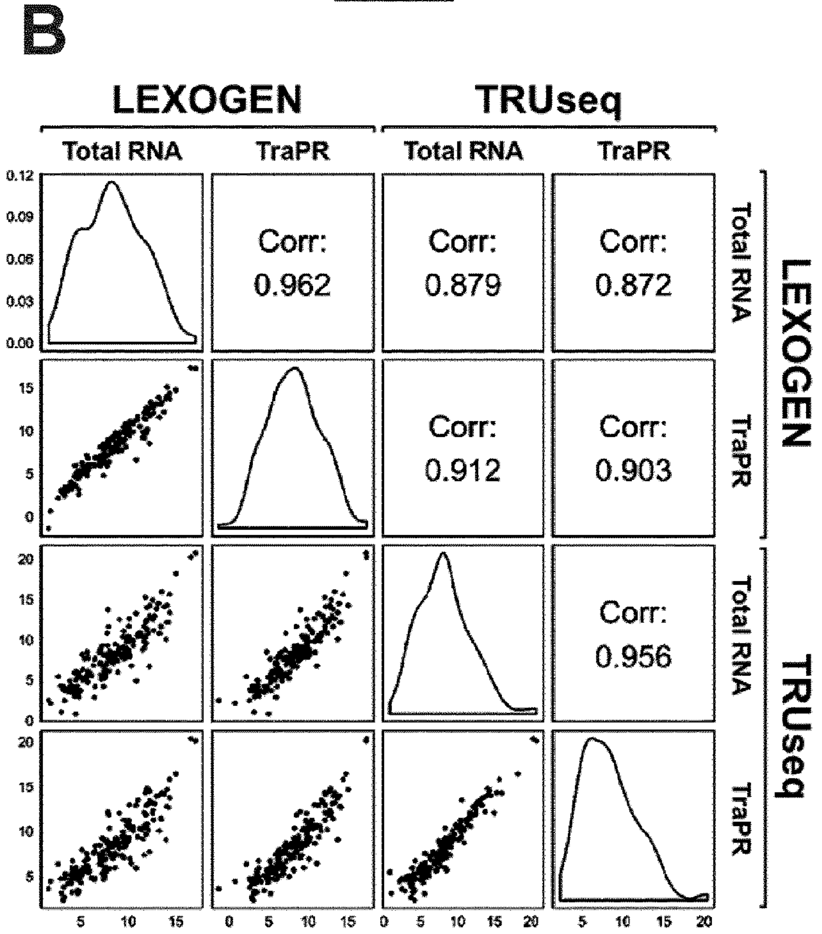

Exploration of sRNAs typifying a tissue- or cell-type-specific state or pathological condition, is usually achieved via deep-seq. Once robust sRNA markers of this state/condition are identified, they can then be used in a targeted manner as quantitative indicators of said state/condition. The results presented in FIG. 11A shows that targeted detection of two such miRNAs by RT-qPCR is enriched by two orders-of-magnitude in the RISC-associated sRNA E fraction of mouse plasma, purified according to the method of the invention, compared to input (total RNA).

During the validation of the method according to the invention, as a robust asset to produce high quality sequencing libraries of functional sRNA in complex samples (*Arabidopsis* and *Drosophila*), different cloning strategies were applied. A standardized TRUseq (Illumina) procedure was applied for plant samples (FIG. 5). *Drosophila* samples (FIGS. 5 and 6), on the other hand, were subjected to a custom protocol developed by the Brennecke lab (IMBA, Vienna) specifically for fly ovaries. In both cases, use of the method according to the invention strongly improved the quality and robustness of deep-seq results, also suggesting sample integrity as a key parameter in sRNA library preparation.

We aimed at confirming this hypothesis by comparing yet another commercial cloning kit (produced by Lexogen) with the Illumina TRUseq. The results presented in FIG. 11B show a better correlation (0.903) for miRNA populations between the two protocols if the samples are processed according to the method of the invention, compared to total RNA libraries (0.879). We conclude that the method of the invention is suitable for sRNA cloning using a large array of library preparation protocols, ranging from commercial to custom-designed ones. More generally, it confirms that the key step to obtain robust and high quality sRNA libraries for deep-seq is the sRNA sample preparation, for which the method of the invention has been superior in every aspects (time, complexity, technicality, affordability etc.) to all currently employed approaches.

We conclude that the method of the invention is amenable to high-quality sRNAs preparation suitable for RT-qPCR quantification and deep-seq analysis including, chiefly, of miRNAs. The method according to the invention therefore opens great prospects for improved diagnosis/prognosis in terms of reproducibility and depth, offering the guarantee of consistent and robust detection of qualitative and quantitative variations in complex in a multitude of samples including mammalian plasma.

The invention claimed is:

1. A method for the purification of RNA induced silencing complex (RISC)-associated sRNAs, comprising the following steps:

a) providing a RISC-containing sample derived from a human biological specimen;
b) lysing the sample using a lysis buffer to produce a lysate;
c) selectively removing non RISC-associated nucleic acids from the lysate by loading the lysate onto a column comprising an anion exchange resin for binding of the non-RISC associated nucleic acids; and
d) collecting RISCs comprising RISC-associated sRNAs that are not bound to the anion exchange resin in a solution having a suitable conductivity to retain the non-RISC associated nucleic acids on the anion exchange resin.

2. The method of claim 1, wherein in step d) RISCs are collected by applying an elution buffer to the column.

3. The method of claim 1, wherein in step b) the lysate is further clarified by centrifugation or by filtration.

4. The method of claim 1, wherein the column is a 96 well plate or a microfluidic chip.

5. The method of claim 1, wherein the biological specimen is a RISC-containing sample generated by in vitro, in cellulo or in vivo RISC production.

6. The method of claim 1, further comprising:

e) removing the protein content from the collected RISCs using phenol/chloroform/isoamyl-alcohol extraction; or
f) removing the protein content from the collected RISCs using proteinase K treatment.

7. A method of diagnosing a disease in a subject whose diagnosis or prognosis is characterized by the presence of particular sRNAs specific for the disease, comprising performing the method of claim 1 and analyzing the RISC-associated sRNAs to diagnose or to prognose the disease according to levels of the particular sRNAs.

8. The method of claim 7, wherein the disease is a cancer, a metabolic disorder, an hereditary condition or an infectious disease.

9. The method of claim 2, wherein the elution buffer comprises 20 mM HEPES-KOH (pH 7.9), 10 to 20% (v/v)

glycerol, 1.5 mM $MgCl_2$, 0.2 mM EDTA, 1 mM DTT and a $CH_3CO_2K$ concentration between 400 and 800 mM, to reach a measured conductivity between 30 and 50 mS/$cm^2$.

10. The method of claim 1, wherein in step d) the RISCs are collected by applying an elution buffer to the column, wherein the elution buffer has a measured conductivity between 30 and 50 mS/$cm^2$.

* * * * *